US006875867B2

(12) United States Patent
Brodfuehrer et al.

(10) Patent No.: US 6,875,867 B2
(45) Date of Patent: Apr. 5, 2005

(54) PROCESS FOR PREPARING CHIRAL DIOL SULFONES AND DIHYDROXY ACID HMG COA REDUCTASE INHIBITORS

(75) Inventors: Paul R. Brodfuehrer, Syracuse, NY (US); Thomas R. Sattelberg, Cicero, NY (US); Joydeep Kant, Cherry Hill, NJ (US); Xinhua Qian, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 37 days.

(21) Appl. No.: 10/158,355

(22) Filed: May 30, 2002

(65) Prior Publication Data

US 2003/0018199 A1 Jan. 23, 2003

Related U.S. Application Data

(60) Provisional application No. 60/296,403, filed on Jun. 6, 2001.

(51) Int. Cl.[7] .................. C07D 239/42; C07D 221/16; C07D 213/55; C07D 207/34; C07C 67/327
(52) U.S. Cl. .................. 540/577; 544/297; 546/80; 546/89; 546/93; 546/173; 546/342; 548/502; 548/537; 560/119
(58) Field of Search .................. 560/119, 129; 548/511, 537, 502; 546/80, 89, 93, 173, 339, 342; 544/297; 540/577

(56) References Cited

U.S. PATENT DOCUMENTS 6,620,821 B2 * 9/2003 Robl .................. 514/290

OTHER PUBLICATIONS

Patel, D.V. et al, Journal of Organic Chemistry 57(26), 1992, pp. 7143–7151.*
U.S. Appl. No. 60/211,594.*

Blakemore, Paul R., et al., Synlett Letters, p. 26–28, 1997.

Smith, Amos B., et al., J. Org. Chem. 2000, 65, 3738–3753, 1999.

Blakemore, Paul R., et al, J. Chem. Soc., Perkin Trans. 1, 1999, 955–968.

Bellingham, Richard, et al. Synthesis, Feb. 1996, p. 285–296.

Blakemore, Paul R. et. al. Synthesis 1999, No. 7, 1209–1215.

* cited by examiner

Primary Examiner—Thomas C. McKenzie
(74) Attorney, Agent, or Firm—Burton Rodney

(57) ABSTRACT

A process is provided for preparing chiral diol sulfones of the structure

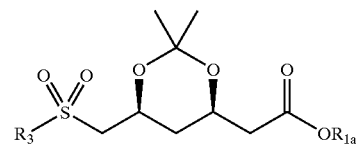

where $R_3$ is preferably

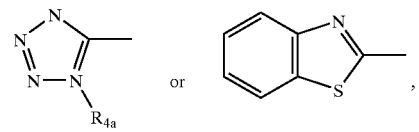

where $R_{4a}$ is preferably aryl such as phenyl, and $R_{1a}$ is preferably alkyl such as t-butyl, which are intermediates used in preparing HMG CoA reductase inhibitors.

6 Claims, No Drawings

PROCESS FOR PREPARING CHIRAL DIOL SULFONES AND DIHYDROXY ACID HMG COA REDUCTASE INHIBITORS

This application claims priority from U.S. Provisional Application No. 60/296,403 filed Jun. 6, 2001 which is incorporated herein by reference.

FIELD OF THE INVENTION

The present invention relates to a novel process for the preparation of chiral diol sulfones which are key intermediates in the synthesis of dihydroxy acid HMG CoA reductase inhibitors and lactones thereof, and to a process for preparing HMG CoA reductase inhibitors employing such intermediates.

SUMMARY OF THE INVENTION

The present invention is directed to the synthesis of a chiral sulfone intermediate (prepared from Kaneka alcohol preferably via triflate and sulfide intermediates) which is used in preparing a dihydroxy acid HMG CoA reductase inhibitor or lactone thereof. In one aspect of the process of the invention, a Julia-Kocienski olefination reaction is employed wherein the chiral sulfone intermediate is reacted with a carboxylaldehyde to form the desired trans intermediate which may be isolated in high yield and optical purity and which may be converted to the final HMG CoA reductase inhibitor.

DESCRIPTION OF THE INVENTION

In accordance with the present invention, a process is provided for preparing chiral sulfones, which are intermediates for use in preparing dihydroxy acid (or lactone thereof) HMG CoA reductase inhibitors which are useful as anti-cholesterol agents as described hereinafter.

The process of the invention includes the steps of forming a novel chiral sulfone 1 having the structure

1

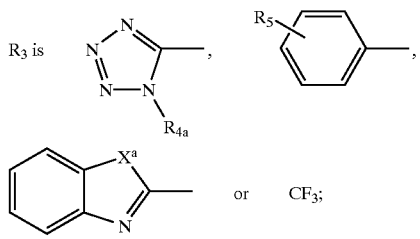

wherein $R_{1a}$ is alkyl, cycloalkyl, arylalkyl, aryl or carbonylbenzyloxy (CbZ);

$R_3$ is

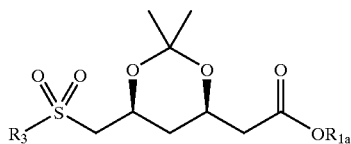

where $R_{4a}$ is alkyl, aryl, arylalkyl or cycloalkyl,
$R_5$ is H, alkyl, aryl, arylalkyl, $CF_3$, halo or $NO_2$ and
$X^a$ is O or S;

by treating a solution of sulfonate of the structure 2

2

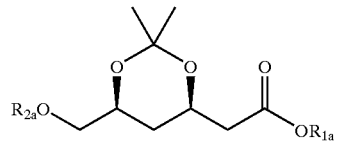

where $R_{2a}$ is $SO_2CF_3$, $SO_2CH_3$, or $SO_2$ $(C_6H_5)$—$_p$—$CH_3$, with a thiol of the structure 3

$R_3SH$   3 to provide novel chiral sulfide 4

4

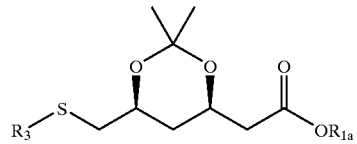

and oxidizing chiral sulfide 4 with hydrogen peroxide or other oxidant in the presence of an appropriate catalyst, such as ammonium heptamolybdate, to provide the novel chiral sulfone 1.

A preferred embodiment of the process of the invention for preparing preferred chiral sulfone intermediate 1a 1a

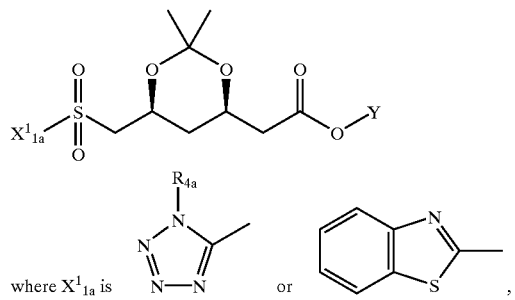

where $R_{4a}$ is aryl, alkyl, arylalkyl or cycloalkyl (where $R_{4a}$ is preferably phenyl), and Y is alkyl, aryl, arylalkyl or CbZ, includes the steps of treating a solution of triflate 2a 2a

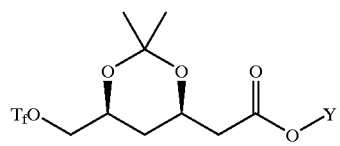

with a tetrazole-thiol or benzothiazole-thiol of the structure 3a or 3b

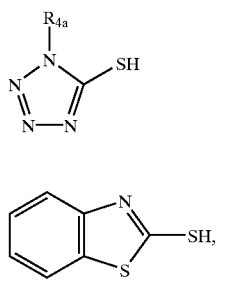  3a

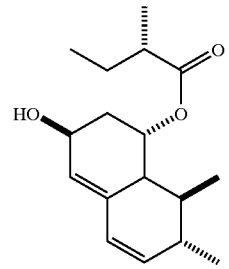  (a)

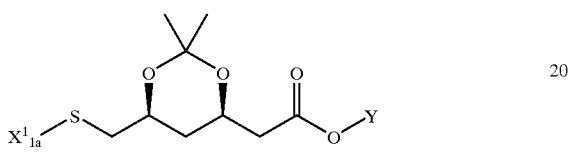  3b such as 1-phenyl-1H-tetrazole-5-thiol, to provide the novel chiral sulfide 4a

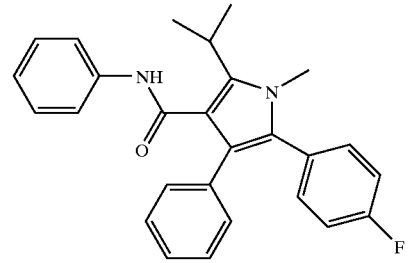  (b)

and oxidizing chiral sulfide 4a with hydrogen peroxide or other oxidant in the presence of an appropriate catalyst, such as ammonium heptamolybdate, to provide the novel chiral sulfone 1a.

The triflate 2a may be prepared by treating chiral alcohol 2b

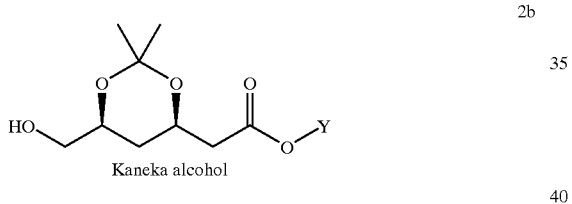  2b

Kaneka alcohol

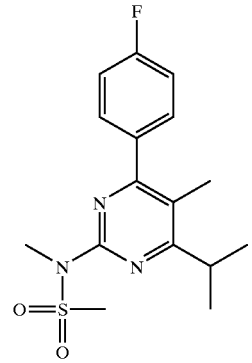  (c)

(where Y is preferably alkyl, and most preferably t-butyl) with triflic anhydride (trifluoromethanesulfonic anhydride) and an organic base, preferably triethylamine or diisopropylethylamine, in an organic solvent such as dichloromethane at low temperature (for example, from about −45 to about 0° C.) to afford novel triflate 2a.

Other sulfonate starting materials 2 may be prepared starting with Kaneka alcohol 2b and reacting same with an appropriate anhydride 2c

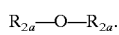  2c

In addition, in accordance with the present invention, a process is provided for preparing trans olefin 6

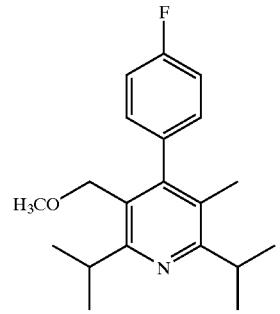  (d)

6

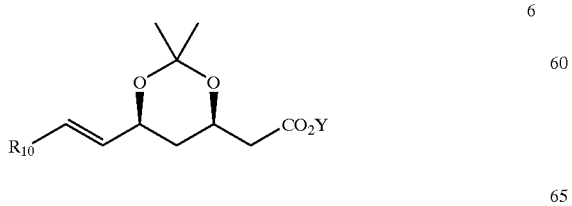

where $R_{10}$ is a hydrophobic anchor or residue of an HMG CoA reductase inhibitor and may, for example, be

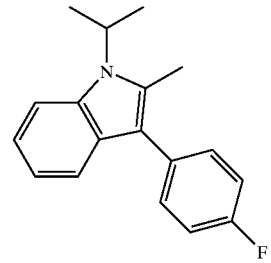  (e)

-continued (f)
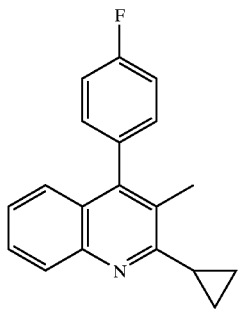

(g)
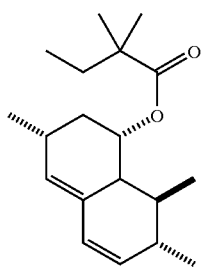

(h)
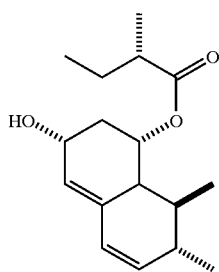

(i)
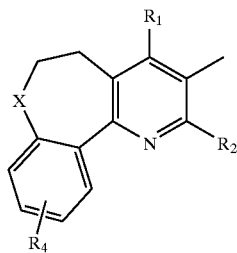

where X is CH₂, O, S or NR₇, preferably CH₂;
R₁ and R₂ are the same or different and are independently selected from alkyl, arylalkyl, cycloalkyl, alkenyl, cycloalkenyl, aryl, heteroaryl or cycloheteroalkyl (R₁ is preferably p-F-phenyl and R₂ is preferably alkyl, most preferably isopropyl);
R₄ is H, halogen, CF₃, hydroxy, alkyl, alkoxy, alkanoylamino, aroylamino, or cyano (R₄ is preferably H);
R₇ is H, alkyl, aryl, alkanoyl, aroyl, or alkoxycarbonyl.
The trans-olefin 6 is prepared via a Julia-Kocienski olefination, which includes the steps of reacting aldehyde 7

7

with chiral sulfone 1 in the presence of LiHMDS or NaHMDS or other base at a low temperature (for example, within the range from about −78 to about −30° C.) to provide trans olefin 6.

The trans-olefin 6 may be used to form a dihydroxy acid (or lactam thereof) HMG CoA reductase inhibitor by subjecting trans-olefin 6 to acidic conditions to remove the acetonide and form diol 8

8
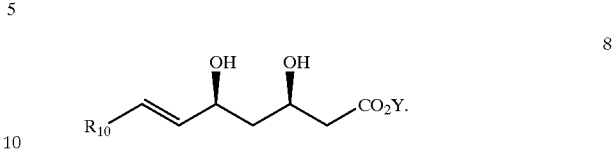

The diol 8 may be treated with a base such as an alkali metal hydroxide (for example, NaOH) to form the corresponding alkali metal salt 9

9
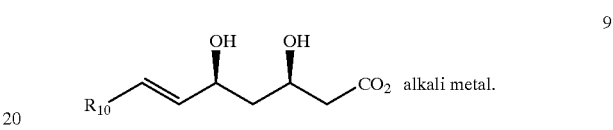

The salt 9 may be converted to the free acid 10 by treating 9 with an acid such as TFA, HCl, to give acid 10

10
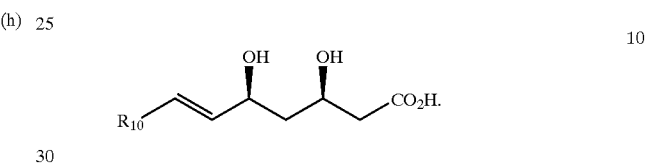

The alkenyl double bond in acid 10 may be hydrogenated (H₂/Pd/C) to provide the saturated alkyl acid 11

11
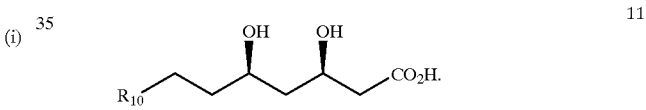

The lactone 13 may be prepared

13
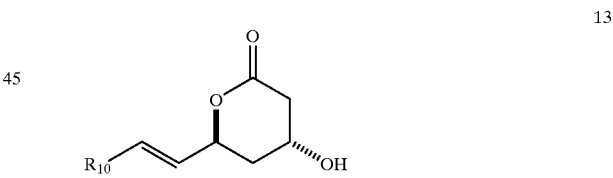

by treating the trans-olefin 6 under acid conditions (for example TFA, HCl) to effect conversion to lactone 13. The saturated derivative of lactone 13 may be obtained by catalytic (Pd/C, Pt/C, Pd(OH)₂) hydrogenation of 13 to 14

14
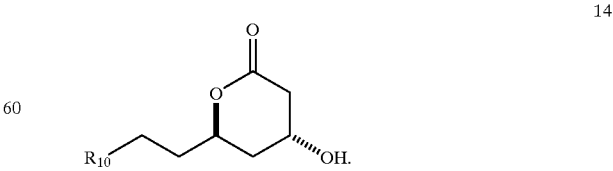

Lactones 13 and 14 may be converted to the corresponding diols by saponification of 13 or 14 with aqueous base to form the salt 9 or 12

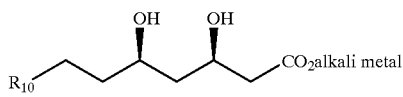

It will be appreciated that the process of the invention may be employed to prepare pravastatin, atorvastatin, cerivastatin, fluvastatin, rosuvastatin, nisvastatin (pitavastatin), simvastatin, lovastatin and other dihydroxy acid or lactone HMG CoA reductase inhibitors.

The aldehyde 7 starting material is obtained by reducing the corresponding ester 7a

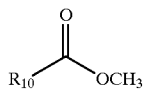

with Red-Al or other reducing agent such as lithium aluminum hydride or Dibal, followed by oxidation with 2,2,6,6-tetramethyl-1-piperidinyloxy (TEMPO) along with Na hypochlorite to give aldehyde 7.

In addition, in accordance with the present invention, a preferred process is provided for preparing the preferred trans-olefin 6a

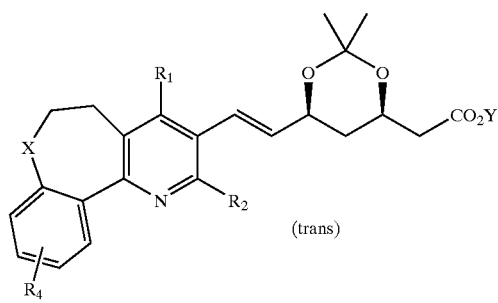

via a Julia-Kocienski olefination which includes the step of reacting pyridine carboxylaldehyde 7b

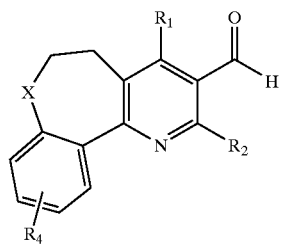

with chiral sulfone 1a in the presence of LiHMDS or NaHMDS or other base at a low temperature (for example, within the range from about −78 to about −30° C.) to provide trans-olefin 6a.

The trans-olefin 6a may be used to form a dihydroxy acid (or lactone thereof) HMG CoA reductase inhibitor 8a by subjecting trans-olefin 6a to acidic conditions to remove the acetonide and form diol 8a

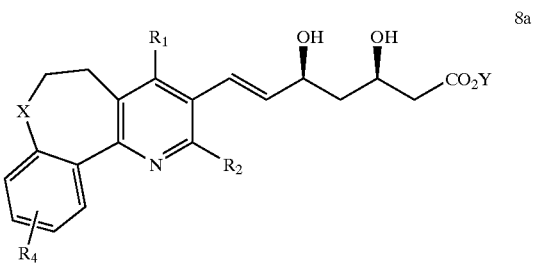

and treating diol 8a with a base such as an alkali metal hydroxide (such as NaOH) to form alkali metal salt 9a

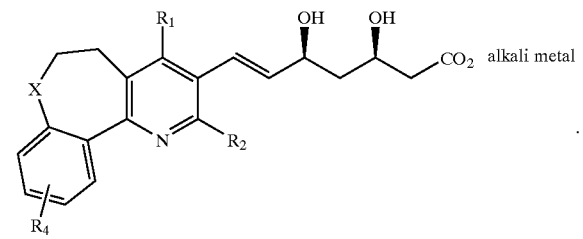

The free acid is formed by treating alkali metal salt 9a with an acid such as HCl to give acid 10a

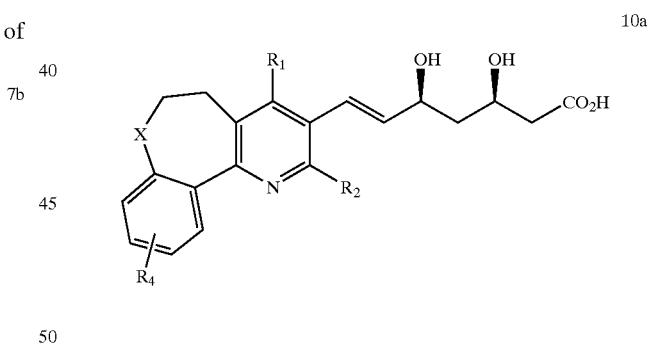

Free acid 10a may be treated with arginine to form the arginine salt 9b

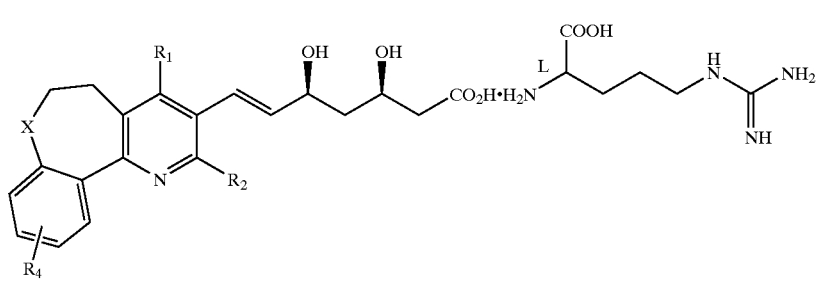

The trans olefin 6a may be converted to its corresponding lactone by treating 6a with acid such as TFA or HCl.

The pyridine carboxyl aldehyde 7b is obtained by reduction of the corresponding ester 12a

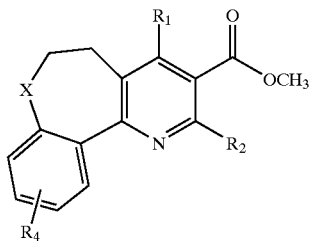

12a with Red-Al or other reducing agent such as lithium aluminum hydride or Dibal followed by oxidation with 2,2,6,6-tetramethyl-1-piperidinyloxy (TEMPO) along with NaOCl to give pyridine carboxylaldehyde 7b.

In addition, in accordance with the present invention, the following intermediates prepared by the process of the invention are novel compounds:

I

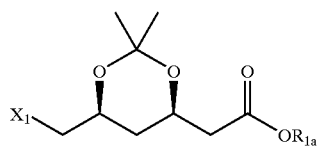

where $X_1$ is $CF_3SO_2O—$, $CH_3SO_2O^-$ or $p-CH_3—(C_6H_5)SO_2O—$; or $R_3S—$ or $R_3SO_2—$
where $R_3$ is

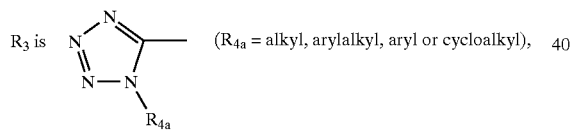  ($R_{4a}$ = alkyl, arylalkyl, aryl or cycloalkyl),

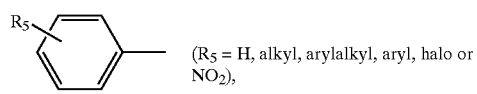  ($R_5$ = H, alkyl, arylalkyl, aryl, halo or $NO_2$),

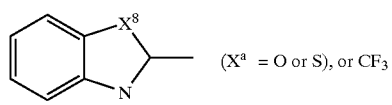  ($X^a$ = O or S), or $CF_3$ and $R_{1a}$ is alkyl, cycloalkyl, arylalkyl, aryl or CbZ.

II

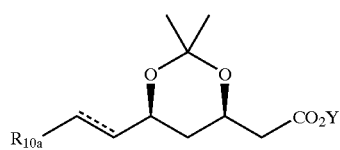

where ⤳ represents a single bond or a double bond,

Y is alkyl, aryl, arylalkyl or CbZ, and $R_{10a}$ is (a)

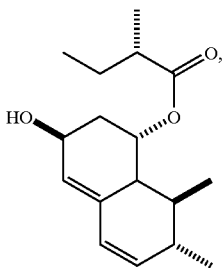

(b)

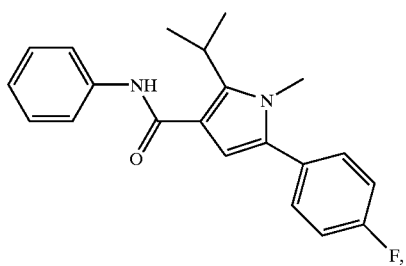

(c)

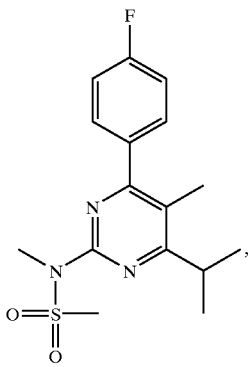

(d)

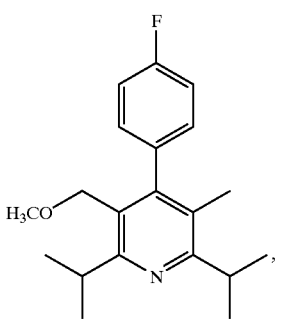

(e)

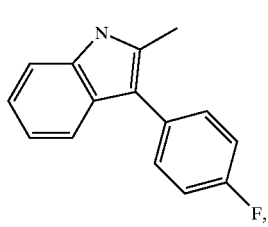

-continued (f)

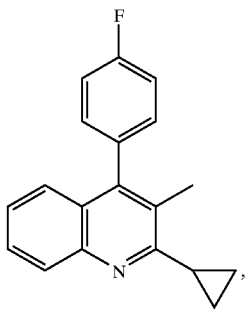

(g)

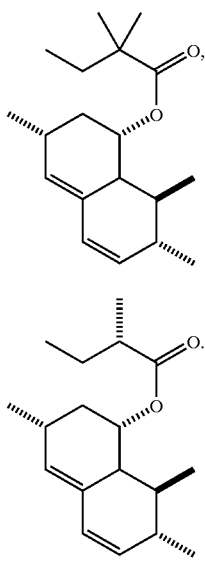

(h)

III

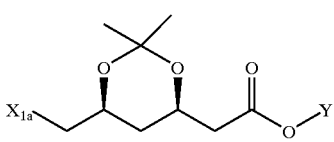

where $X_{1a}$ is

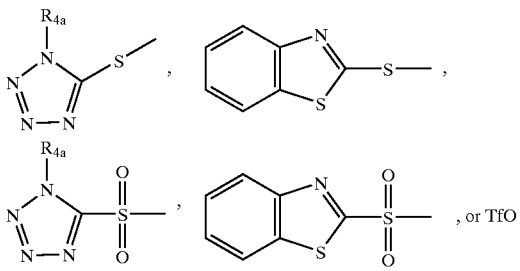, or TfO wherein $R_{4a}$ is aryl, alkyl, arylalkyl, or cycloalkyl; and Y is alkyl, aryl, arylalkyl or CbZ.

IV $$R_{10}-\overset{\overset{O}{\|}}{CH}.$$

DETAILED DESCRIPTION OF THE INVENTION

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example, acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1–C4) alkyl or arylsulfonic acids which are unsubstituted or substituted, for example by halogen, for example methanesulfonic acid or p-toluenesulfonic acid.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, cycloheteroalkyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

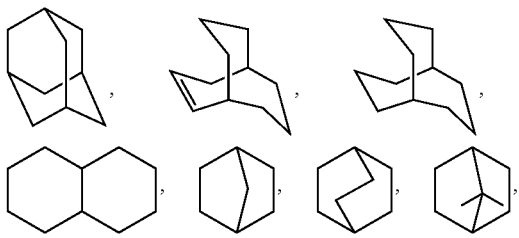

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, heteroaryl, cycloheteroalkyl, amino, alkylamino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted with 1 or 2 substituents as defined above for "alkyl", such as, for example, alkyl, halo, hydroxy, alkoxy and/or cycloalkyl.

Where alkenyl groups as defined above and alkynyl groups as defined above, respectively, have single bonds for attachment at two different carbon atoms, they are termed "alkenylene groups" and "alkynylene groups", respectively, and may optionally be substituted with 1 or 2 substituents as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

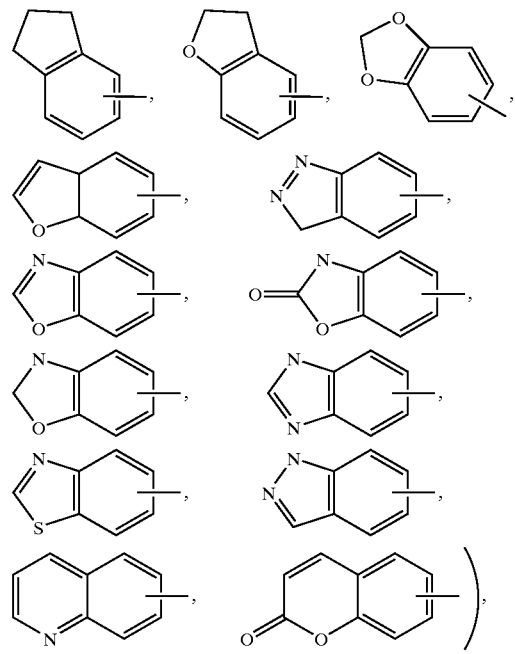

and may be optionally substituted through available carbon atoms with 1, 2, or 3 groups selected from hydrogen, halo, haloalkyl, alkyl, haloalkyl, alkoxy, halophenyl, benzoyloxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, alkanoyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio, "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as

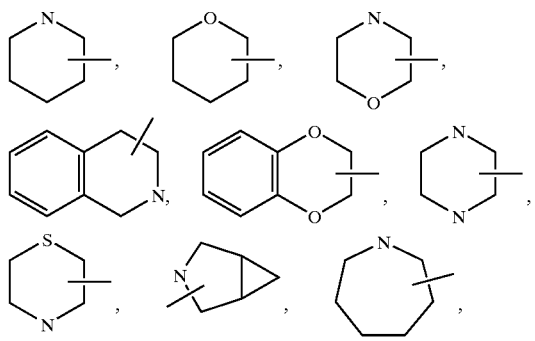

and the like. The above groups may include 1 to 4 substituents such as alkyl, halo, oxo and/or any of of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

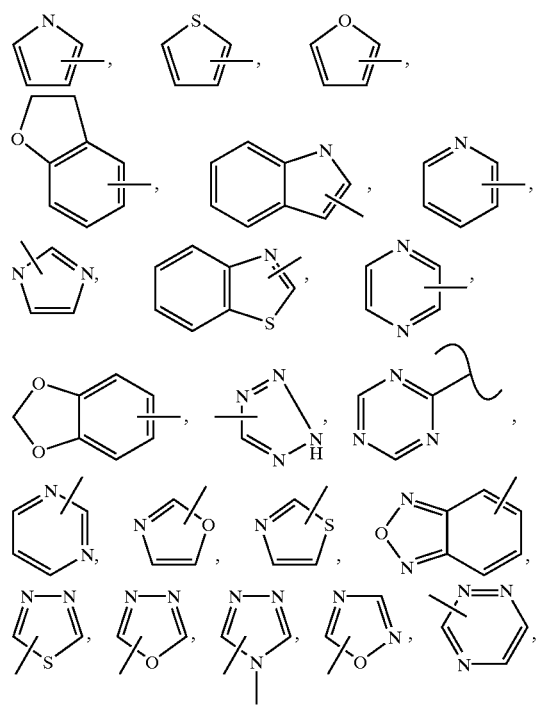

and the like.

The term "cycloheteroalkylalkyl" as used herein alone or as part of another group refers to cycloheteroalkyl groups as defined above linked through a C atom or heteroatom to a $(CH_2)_r$ chain.

The term "heteroarylalkyl" or "heteroarylalkenyl" as used herein alone or as part of another group refers to a heteroaryl group as defined above linked through a C atom or heteroatom to a $-(CH_2)_r-$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkoxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

All stereoisomers of the compounds prepared herein are contemplated, either in admixture or in pure or substantially pure form. The compounds can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. In addition, prodrug esters which are known in the art for carboxylic and phosphorus acid esters such as methyl, ethyl, benzyl and the like.

Examples of such prodrug esters include

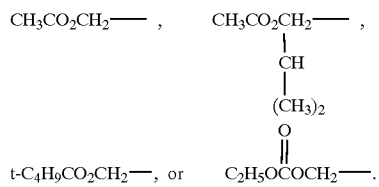

Other examples of suitable prodrug esters include

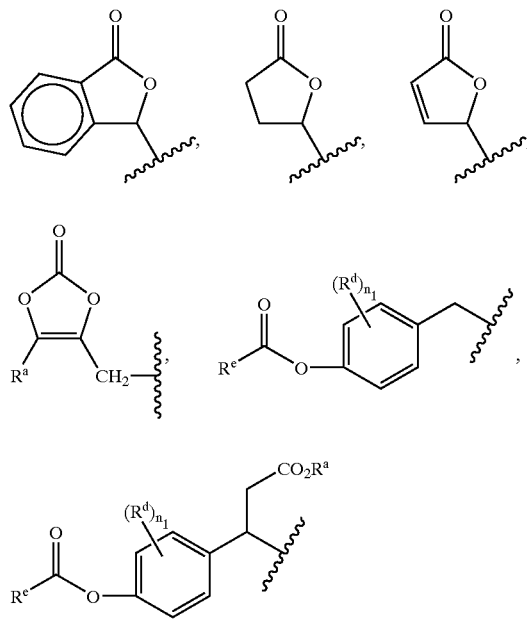

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the final compounds are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl) aminomethane (TRIS), N-methyl glucosamine (NMG), triethanolamine and dehydroabietylamine.

The term "residue of an HMG CoA reductase inhibitor" as emloyed herein refers to the portion of the HMG CoA reductase inhibitor or hydrophobic anchor attached to the dihydroxy acid moiety or the lactone moiety.

As set forth in the following Schemes, the process of the invention for the preparation of chiral diol sulfones and dihydroxy acid HMG CoA reductase inhibitors involves the following chemical reactions.

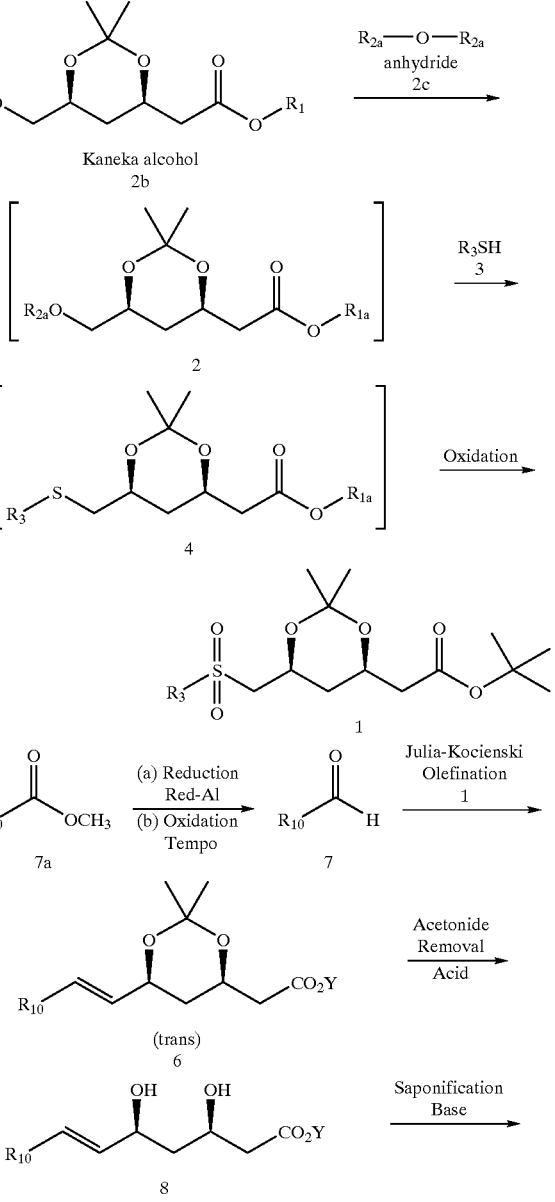

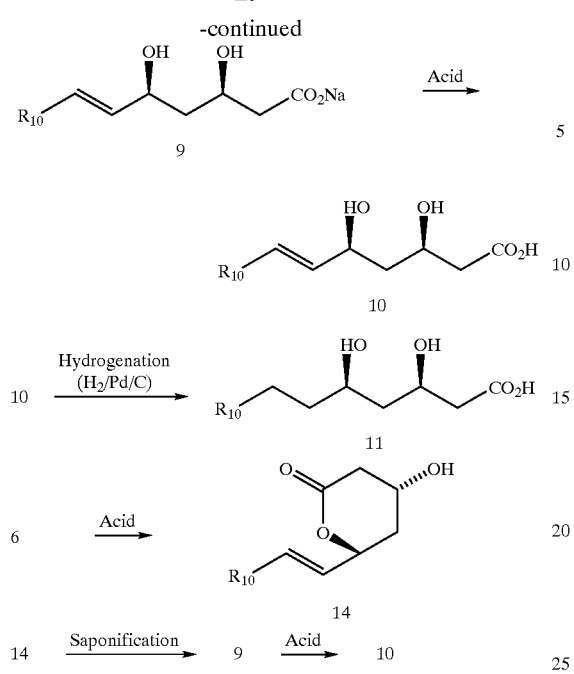

The above methodology can be used to prepare HMG CoA reductase inhibitors including, but not limited to, pravastatin, lovastatin, simvastatin, nisvastatin (pitavastatin), rosuvastatin (Astra Zeneca), fluvastatin, cerivastatin and atorvastatin.

Scheme 1 depicts a method for preparing novel chiral sulfone diol 1 and the HMG CoA reductase inhibitor of formula 8 using the Julia-Kocienski olefination reaction employing carboxylaldehyde 7 and chiral sulfone 1, in a molar ratio within the range from about 0.5:1 to about 2:1, preferably from about 0.8:1 to about 1.5:1. The desired trans intermediate 6 is isolated in high yield and optical purity which is converted to the final product of the invention. As will be seen, the chiral sulfone 1, a key intermediate in the Julia-Kocienski step, is prepared in three steps starting from the commercially available Kaneka alcohol (2b) via diol 2 and sulfide intermediate 4.

Referring to Scheme 1, treatment of commercially available chiral alcohol 2b with anhydride 2c (employing a molar ratio of 2b:2c within the range from about 0.5:1 to about 2:1, preferably from about 0.7:1 to about 1.5:1), and base such as diisopropylethylamine (DIPEA), triethylamine or lutidine, in dichloromethane at low temperature (for example −45 to −15° C.) affords 2. Other pyridine or amine bases may be employed. Compound 2 (without being isolated) is carried

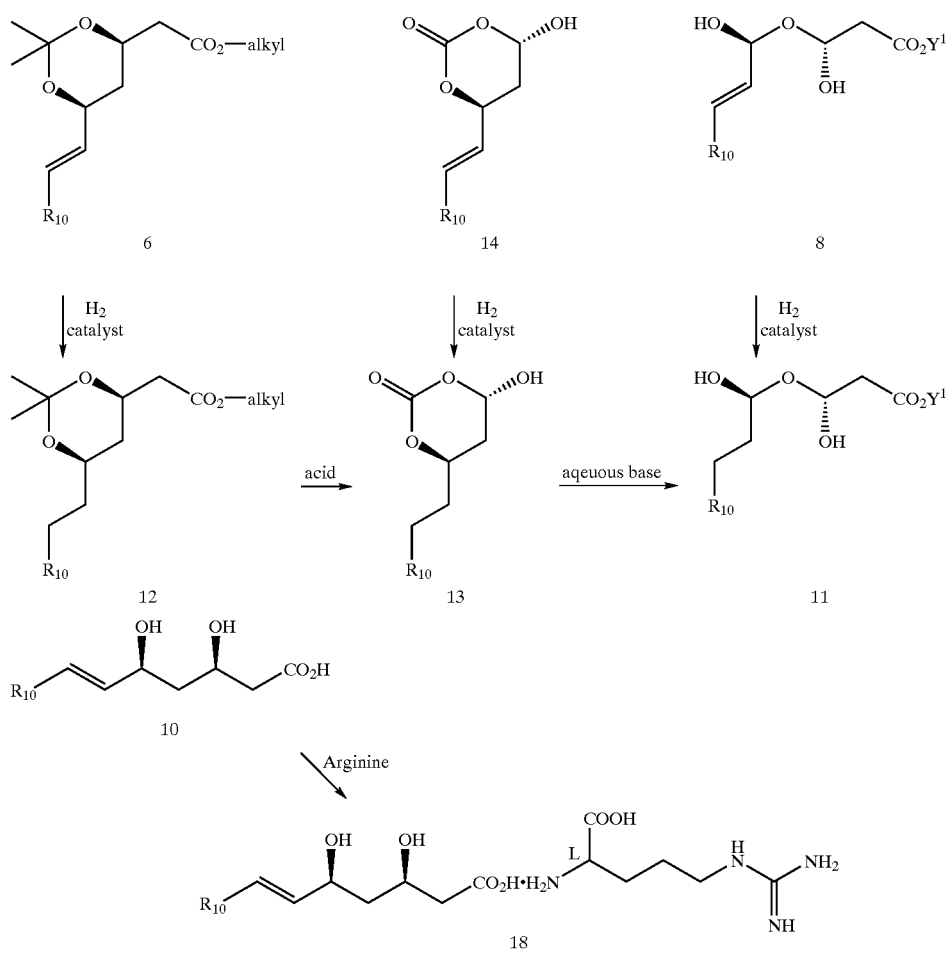

onto the next step without further purification. A methylene chloride (or other appropriate solvent) solution of 2 is treated with thiol 3 (in a molar ratio of 2:3 within the range from about 0.5:1 to about 2:1 preferably from about 0.8:1 to about 1.5:1) to provide the chiral sulfide 4 which is oxidized with hydrogen peroxide in the presence of catalytic ammonium heptamolybdate tetrahydrate (or other metal catalyst such as known vanadium complex catalysts) to give crystalline sulfone 1. Other oxidant, such as m-chloroperbenzoic acid (MCPBA) or Oxone® (potassium peroxymonosulfate) may be employed.

Addition of base such as LiHMDS or NaHMDS to a mixture of sulfone 1 and carboxylaldehyde 7 (in a molar ratio of base:1 within the range from about 0.5:1 to about 2:1, preferably from about 0.8:1 to about 1.5:1) in THF at low temperature (−78 to −30° C.) provides trans olefin 6 in high diastereoselectivity.

The aldehyde 7 is obtained as a crystalline solid from the corresponding ester 7a. Reduction of ester 7a with Red-Al, lithium aluminum hydride or Dibal, followed by oxidation with TEMPO (2,2,6,6-tetramethyl-1-piperidinyloxy) and NaOCl gives aldehyde 7 in high yield. Compound 8 is prepared in a one pot procedure starting from 6 without isolating any intermediates. Removal of acetonide under acidic condition (TFA, HCl) (employing a molar ratio of acid:6 within the range from about 0.5:1 to about 2:1, preferably from about 0.8:1 to about 1.5:1) provides diol 8 which upon further treatment with sodium hydroxide or other alkali metal hydroxide gives the corresponding salt of the acid 9 of the invention. Subsequent treatment of 9 with acid (employing a molar ratio of acid:9 within the range from about 0.5 to about 2:1, preferably from about 0.8:1 to about 1.5:1) forms acid 10. Addition of arginine (molar ratio arginine:10 from about 0.5:1 to about 2:1, preferably from about 0.8:1 to about 1.5:1) produces crystalline arginine 18 (Scheme 1A).

Treatment of 6 under acidic conditions (e.g. TFA, HCl) (employing a molar ratio of acid:6 within the range from about 0.5:1 to about 2:1, preferably from about 0.8:1 to about 1.5:1) effects the conversion of 6 to lactone 14. Saponification of 14 to give 9 can be effected by treatment of 14 with aqueous base ($Y^1OH$ where $Y^1$ is alkali metal or alkaline earth metal) (molar ratio of base:14 within the range from about 0.5:1 to about 2:1, preferably from about 0.8:1 to about 1.5:1) which can be subsequently acidified to give acid 10. Additionally, 14 can be treated with an alcohol of the type $Y^1OH$ (molar ratio of alcohol:14 from about 0.5:1 to about 2:1, preferably from about 0.8:1 to about 1.5:1) under basic conditions to form the corresponding esters 8.

As seen in Reaction Schemes 1 and 1A, the saturated derivatives of compound 10 (where ∿ is $CH_2$—$CH_2$) are obtained by catalytic (Pd/C, Pt/C, Pd(OH)$_2$) hydrogenation of 10, 6, 14 or 8 to afford 11, 13, 13 or 11, respectively. Compound 12 may be converted to 13 via acid treatment and 13 to 11 via base treatment.

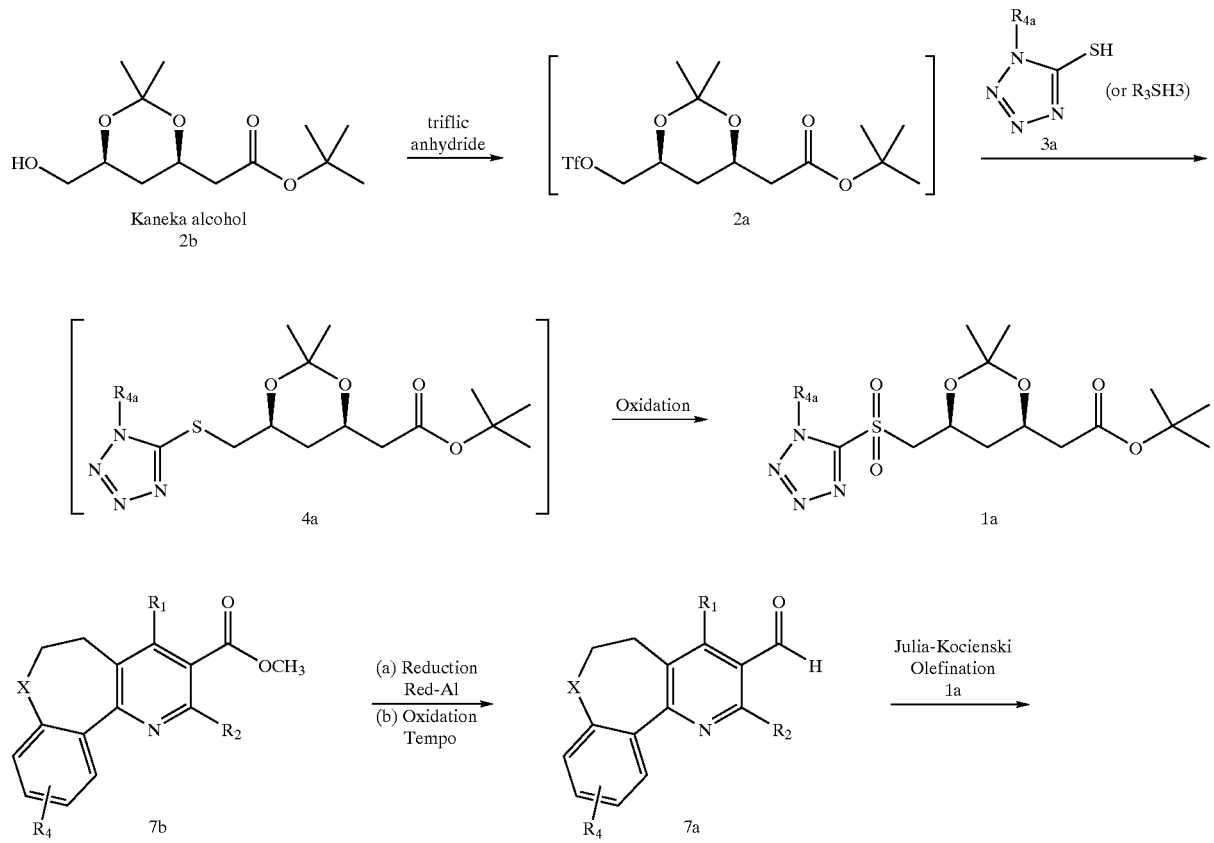

-continued
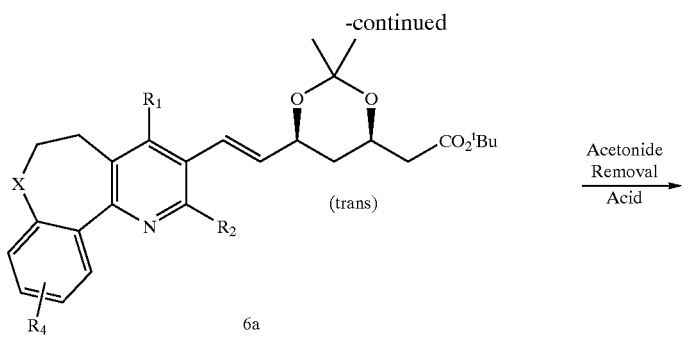
Acetonide Removal
Acid
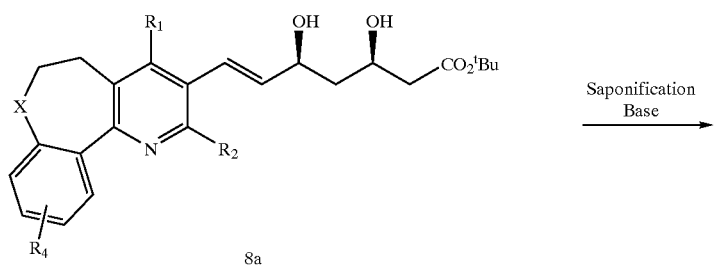
Saponification Base
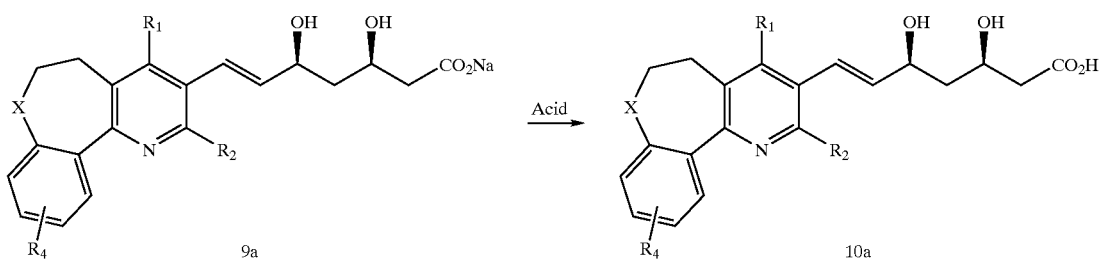
Acid
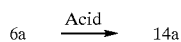
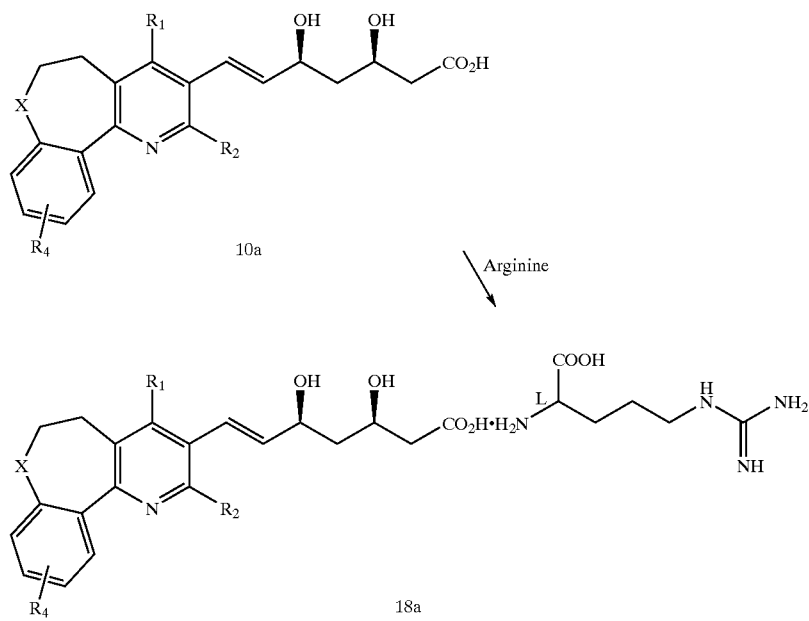
Arginine

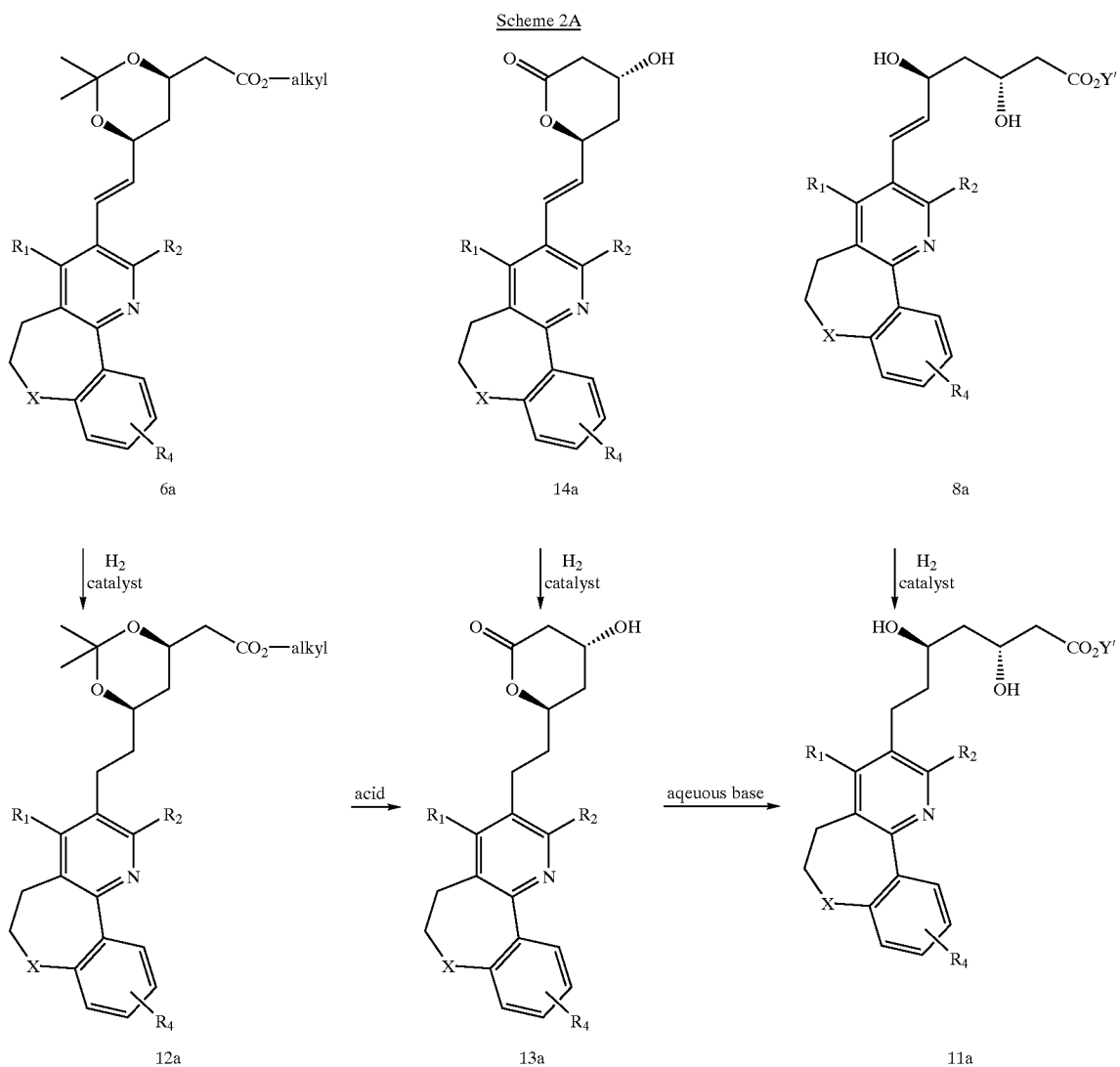

Scheme 2A

Scheme 2 depicts a preferred method for preparing chiral sulfone intermediate 1a and the HMG CoA reductase inhibitor of formula 10a, ester thereof 8a and salts thereof 9a, using the Julia-Kocienski olefination reaction employing carboxylaldehyde 7a and chiral sulfone 1a. The desired trans intermediate 6a is isolated in high yield and optical purity which is converted to the final product of the invention. As will be seen, the chiral sulfone 1a, a key intermediate in the Julia-Kocienski step, is prepared in three steps starting from the commercially available Kaneka alcohol 2b via triflate 2a and sulfide intermediate 4a.

Referring to Scheme 2, treatment of commercially available chiral alcohol 2b with triflic anhydride (employing a molar ratio of anhydride:2b within the range from about 0.5:1 to about 2:1, preferably from about 0.8:1 to about 1.5:1) and triethylamine, DIPEA or lutidene, in dichloromethane at low temperature (for example −45 to 0° C.) affords triflate 2a. Other pyridine or amine bases may be employed. Triflate 2a (without being isolated) is carried onto the next step without further purification. A methylene chloride (or other appropriate solvent) solution of triflate 2a is treated with tetrazole-5-thiol 3a (or benzothiazole-thiol 3b or other $R_3SH3$) (employing a molar ratio of 2a:3a (or other thiol) within the range from about 0.5:1 to about 2:1, preferably from about 0.8:1 to about 1.5:1) to provide the chiral sulfide 4a (or the corresponding benzothiazole or $R_3$ sulfide) which is oxidized with hydrogen peroxide in the presence of catalytic ammonium heptamolybdate tetrahydrate (or other metal catalyst such as vanadium complexes) to give crystalline sulfone 1a. Other oxidant, such as m-chloro-perbenzoic acid (mCPBA) or Oxone® may be employed.

Addition of base such as LiHMDS or NaHMDS to a mixture of sulfone 1a and carboxylaldehyde 7a (employing a molar ratio of 7a:1a within the range from about 0.5:1 to about 2:1, preferably from about 0.8:1 to about 1.5:1) in THF at low temperature (−78 to −40° C.) provides trans olefin 6a in high diastereoselectivity (>99%).

The aldehyde 7a is obtained as a crystalline solid form the corresponding ester 7b. Reduction of ester 7b with Red-Al, lithium aluminum hydride or Dibal followed by oxidation with TEMPO (2,2,6,6-tetramethyl-1-piperidinyloxy) and NaOCl gives aldehyde 7a in high yield. Compound 8a is prepared in a one pot procedure starting from 6a without isolating any intermediates. Removal of acetonide under acidic condition (TFA, HCl) (employing a molar ratio of acid:6a within the range from about 0.5:1 to about 2:1, preferably from about 0.8:1 to about 1.5:1) (employing a solvent such as ethyl acetate, isopropyl alcohol or tetrahydrofuran) provides diol 8a which upon further treatment with sodium hydroxide or other alkali metal hydroxide gives the corresponding salt (9a) of the acid 10a. Subsequent treatment of 9a with acid forms acid 10a. Addition of arginine to acid 10a (molar ratio of arginine:10a from about 0.5:1 to about 2:1, preferably from about 0.8:1 to about 1.5:1) (with or without seeding with final arginine salt) produces crystalline arginine salt 18a.

Treatment of 6a under acidic conditions (e.g. TFA, HCl) effects the conversion of 6a to lactone 14a (employing a molar ratio of acid:6a within the range from about 0.5:1 to about 2:1, preferably from about 0.8:1 to about 1.5:1). Saponification of 14a to 9a (where $Y^1$ is alkali metal, or alkaline earth metal) can be effected by treatment of 14a with aqueous base (molar ratio of base:14a from about 0.5:1 to about 2:1, preferably from about 0.8:1 to about 1.5:1) which can be subsequently acidified to give 10a. Additionally, 14a can be treated with an alcohol of the type $Y^1OH$ (molar ratio of alcohol:14a from about 0.5:1 to about 2:1, preferably from about 0.8:1 to about 1.5:1) under basic conditions to form the corresponding esters of 8a.

As seen in Reaction Schemes 2 and 2A, the saturated derivatives of compound 10a (where ⟋ is $CH_2$—$CH_2$) are obtained by catalytic (Pd/C, Pt/C, Pd(OH)$_2$) hydrogenation of 10a, 6a, 14a or 8a to afford 11a, 13a, 13a or 11a, respectively. Compound 12a may be converted to 13a via acid treatment and 13a to 11a via base treatment.

Compounds containing dihydroxy acid HMG-CoA binding domain side chains may be prepared in homochiral form, which is preferred, or may be prepared as racemic mixtures (3S*, 5R*) and may later be resolved to obtain the 3S, 5R isomer.

The 3-hydroxy-3-methyl-glutaryl coenzyme A (HMG-CoA) reductase inhibitors prepared herein are useful in inhibiting cholesterol biosynthesis and/or in lowering triglycerides, in a manner similar to atorvastatin, pravastatin, simvastatin, lovastatin, cerivastatin, rosuvastatin (Astra Zeneca ZD4522), fluvastatin, pitavastatin and the like.

A pharmaceutical composition may be prepared containing at least one of the HMG CoA reductase inhibitor compounds in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations. Such dosage forms contain from 0.1 to 1500 mg of active compound per dosage, for use in the treatment. The dose to be administered depends on the unitary dose, the symptoms, and the age and the body weight of the patient.

The HMG CoA reductase inhibitor compounds can be administered in a similar manner as known compounds suggested for use in inhibiting cholesterol biosynthesis, such as pravastatin, lovastatin, simvastatin, visastatin, atorvastatin, cerivastatin, fluvastatin, itavastatin, and the like, in mammalian species such as humans, dogs, cats and the like. Thus, the compounds may be administered in an amount from about 0.1 to 500 mg in a single dose or in the form of individual doses from 1 to 4 times per day, preferably 0.2 to 100 mg daily or in sustained release form.

The HMG CoA reductase inhibitors prepared herein may be employed in combination with all therapeutic agents which are useful in combination with HMG CoA reductase inhibitors.

Thus, where desired, the compounds prepared herein may be used in combination with one or more hypolipidemic agents or lipid-lowering agents, or lipid agents, or lipid modulating agents, and/or one or more other types of therapeutic agents including antidiabetic agents, anti-obesity agents, antihypertensive agents, platelet aggregation inhibitors, anti-Alzheimer's agents, anti-osteoporosis agents, and/or hormone replacement therapeutic agents, which may be administered orally in the same dosage form, in a separate oral dosage form or by injection.

The hypolipidemic agent or lipid-lowering agent or other lipid agent or lipid modulating agent which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, cholesteryl ester transfer protein inhibitors, bile acid sequestrants, and/or nicotinic acid and derivatives thereof In carrying out methods for treating hypercholesterolemia, hyperlipidemia, hyperlipoproteinemia, hypertriglyceridemia, or atherosclerosis, and related diseases, or Alzheimer's disease or osteoporosis, a pharmaceutical composition will be employed containing the compounds prepared herein, with or without other cholesterol lowering agents, osteoporosis agents, Alzheimer's agents, antidiabetic agent(s) and/or anti-hyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 0.1 to about 500 mg of a compound of formula I. The dose for adults is preferably between 0.5 and 1,000 mg per day, which can be administered in a single dose or in the form of individual doses from 1–4 times per day.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following abbreviations are employed in the Examples and elsewhere herein:

Ph=phenyl

En=benzyl i-Bu=iso-butyl

Me=methyl

Et ethyl

TMS=trimethylsilyl

FMOC=fluorenylmethoxycarbonyl

Boc=tert-butoxycarbonyl

Cbz=carbobenzyloxy or carbobenzoxy or benzyloxycarbonyl

DIPEA=diisopropyl ethylamine

PTSH=N-phenylthiotetrazole
PPh₃=triphenylphosphine
NMO=methylmorpholine N-oxide
TPAP=tetrapropylammonium perruthenate
DEAD=diethyl azodicarboxylate
HOAC or AcOH=acetic acid
TFA=trifluoroacetic acid
Et₂NH=diethylamine
NMM=N-methyl morpholine
Oxone®=monopersulfate compound (potassium peroxymono-sulfate)
n-BuLi=n-butyllithium
Pd/C=palladium on carbon
PtO₂=platinum oxide
TEA=triethylamine
EDAC=3-ethyl-3'-(dimethylamino)propyl-carbodiimide hydrochloride (or 1-[(3-(dimethyl)amino)propyl])-3-ethylcarbodiimide hydrochloride)
HOBT or HOBT.H₂O=1-hydroxybenzotriazole hydrate
HOAT=1-hydroxy-7-azabenzotriazole
PyBOP reagent=benzotriazol-1-yloxy-tripyrrolidino phosphonium hexafluorophosphate
DIBAL=diisobutylaluminum hydride
LDA=lithium diisopropylamide
DMPU=1,3-dimethyl-3,4,5,6-tetrahydro-2(1H)-pyrimidinone
AcCN=acetonitrile
LIHMDS=lithium bis(trimethylsilyl)amide
NaHMDS=sodium bis(trimethylsilyl)amide
Red-AL=sodium bis(2-methoxyethoxy)aluminum hydride
mCPBA=m-chloro-perbenzoic acid
min=minute(s)
h or hr=hour(s)
L=liter
mL=milliliter
μL=microliter
g=gram(s)
mg=milligram(s)
mol=moles
mmol=millimole(s)
meq=milliequivalent
RT, rt=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point
Bp=boiling point The following Examples represent preferred embodiments of the invention. Unless otherwise indicated, all temperatures are in degrees Centigrade.

EXAMPLE 1

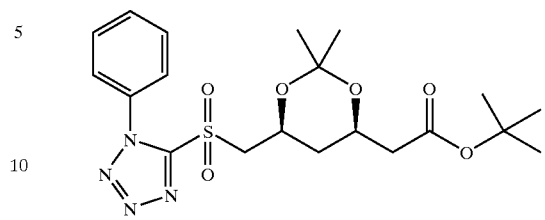

(1a, Scheme 2)

A. Preparation of Triflate

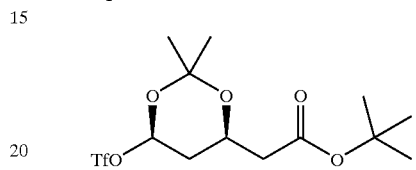

To a 250 mL flask was charged Kaneka alcohol (2b, Scheme 6) (10.0 g, 38.41 mmol), methylene chloride (100 mL), and diisopropylethylamine (14.8 mL, 84.51 mmol) and cooled to −30° C. Triflic anhydride (7.11 mL, 42.25 mmol) was added via a syringe at a rate to maintain the temperature at −35 to −25° C., ~15 min. The reaction mixture was stirred at −30° C. for ~30 min and checked for disappearance of Kaneka alcohol by TLC.

B. Preparation of Sulfide

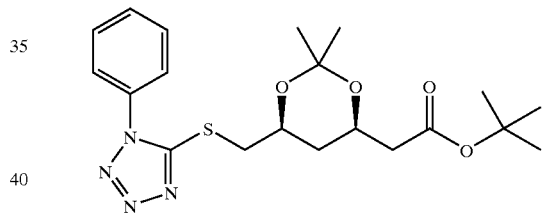

(4a, Scheme 2)

A slurry of 1-phenyl-1H-tetrazole-5-thiol (7.19 g, 40.34 mmol) in methylene chloride (50 mL) was added to the Part A triflate solution. After the reaction was complete, water (100 mL) was added and the mixture was stirred for ~5 min. The phases were separated and the aqueous phase was discarded. The rich organic phase was washed with water (100 mL) for ~5 min and phases separated. The rich organic phase was washed with saturated NaHCO₃ (100 mL) for ~15 min and phases separated. The rich organic phase was concentrated to ~50 mL. The solution was taken to the next step for further transformation.

C. Preparation of Sulfone (1a, Scheme 2)

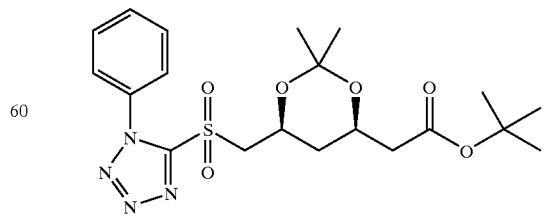

IPA (150 mL) was added to the Part B sulfide solution from the above step. The solution was cooled to 0–5° C. To the stirred solution of sulfide, a solution of (NH$_4$)$_6$ MO$_7$O$_{24}$·4H$_2$O (ammonium heptamolybdate tetrahydrate) (4.75 g, 3.84 mmol) in 30% H$_2$O$_2$ (hydrogen peroxide) was added dropwise during ~15 min, maintaining the temperature of the solution at 0–5° C., then warmed to ambient temperature. The conversion of sulfide to sulfone was monitored by HPLC ~24 h. After completion of the reaction, methylene chloride was distilled out. The pot temperature was maintained at not more than 25° C. The crystal slurry was reconstituted to a volume of ~230 mL with IPA and the resulting slurry was stirred for at least 1 h at 20–22° C. The solid was collected by vacuum filtration, the cake washed with IPA/water (4:1, 25 mL) followed by drying under vacuum at 40° C. to constant weight affording 12.8 g (74%) of the title sulfone as a white crystalline solid.

EXAMPLE 2

Preparation of Pyridine Aldehyde (7a) (Scheme 2)

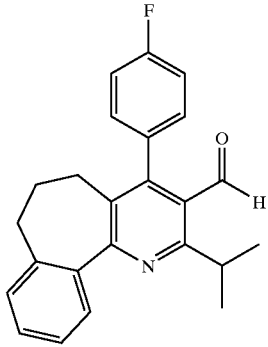

A

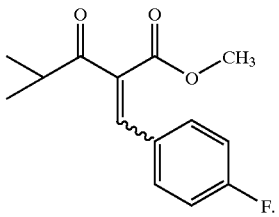

To a mixture of 4-fluoro-benzaldehyde (935.8 g, 7.54 moles) and methyl isobutyryl acetate (1087 g, 7.54 moles) was added piperidine (64.2 g, 0.75 mol), followed by acetic acid (22.6 g, 0.38 mol). The mixture was heated to 80 to 85° C. for about 2 hours. 16 Liters (4×4 L) of toluene was added and mixed with the reaction mixture. The toluene was removed using a rotavapor (50–65° C./20–90 torr), leaving a yellow oil. The yellow oil was dissolved in 5 L MTBE and washed with:

–1×3 L HCl (0.5N)

1×3 L NaHCO$_3$ (saturated soln.)

1×3 L DI water

The MTBE was evaporated off. Thereafter, 1.5 L of MTBE was added and the mixture evaporated to remove water to afford about 1780 g (yield 88%) of title compound as a yellow oil.

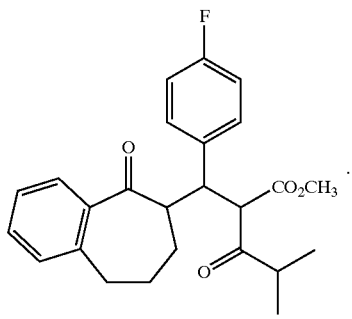

B

To 7.35 L NaHMDS (7.35 moles, 1.05 eq) under N$_2$ (cooled down between –72 to –65° C.) was added a THF (6 L) solution of 1-benzosuborone (1177 g, 7.35 moles, 1.05 eq). The reaction temperature was maintained below –50° C. during the addition. The reaction was then stirred at – between –72 to –65° C. for 1 hour and a solution of compound A (1751.5 g, 7.0 moles, in 6 L THF) was slowly added to the reaction while keeping the temperature below –50° C. After the addition was complete, the reaction was stirred for 2–3 hours between –72 to –65° C. The reaction was quenched with HOAc (1.4 L) between –72 to –50° C. The mixture was allowed to reach RT and saturated ammonium chloride solution (NH$_4$Cl,15 L) was added plus 7 L DI-water, and the mixture agitated for 5–10 min. The aqueous layer was extracted with 1×8 L MTBE. The combined organic layers were washed with water (2×9 L) and brine (1×9 L), then dried. The solvent was removed to afford crude compound B (3.08 kg). The crude compound B was used directly in the next step.

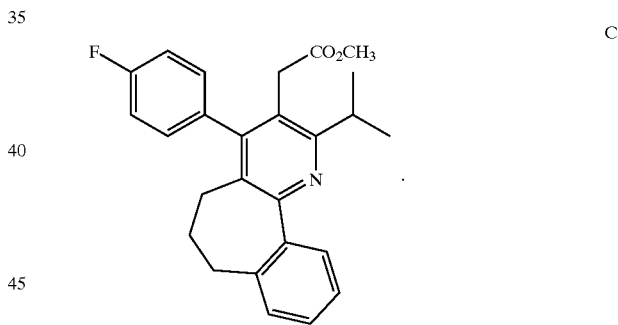

C

To a solution of the crude compound B (3078 g) in aqueous HOAc (16 L) was added ammonium acetate (1446 g), followed by cupric acetate monohydrate (1859 g). The reaction was refluxed between 120 to 124° C. for 12–15 hours. Approximately 90% of the acetic acid was evaporated off to produce a green slurry. The slurry was then mixed with 14 L MTBE (methyl t-butyl ether).

The resulting solution was filtered through a celite pad (177 g celite in a 7"×8", W×H, funnel) and the cake washed with 16 L MTBE. The organic phase was washed with:

2×9 L DI-water, pH of combined wash=4.2

2×3 L NaHCO$_3$, pH of the combined wash=6.4

1×9 L DI-water, pH=6.0.

The solvent was evaporated to produce a black oil (2883 g). 2.5 L of methanol was added and the mixture agitated for approximately 2–3 h. The product was filtered and washed with 2 L of cold methanol (–10 to 0° C.) The product was dried at 40–50° C./~20" of Hg to produce an off-white solid, 793 g, HPLC AP=97.8. Yield=27%

33

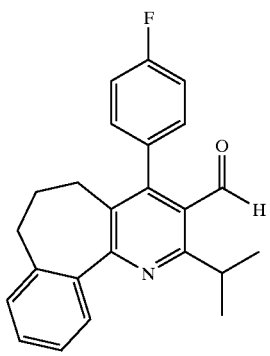

D

To a 500 mL round bottom flask equipped with a magnetic stirrer and a nitrogen inlet was charged

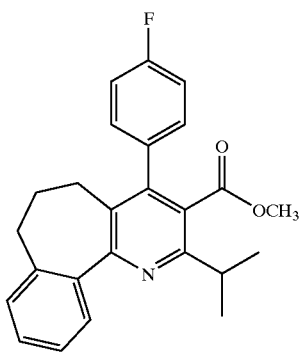

(7b)

(50.0 g, 128.4 mmol) and toluene (170 mL). The mixture was stirred at 20–25° C. until a clear solution was obtained. A solution of 65% Red-Al in toluene (57.8 mL, 192.6 mmol) was added and the reaction mixture was heated to 80° C. until complete as determined by HPLC. The reaction mixture was cooled to ~20° C. and quenched by pouring it into cold (0–5° C.) 20% HCl (495 mL). Phases were separated and the spent toluene phase was discarded. The pH of the aqueous phase was adjusted from <0 to 4–5 with 10N NaOH. Ethyl acetate (500 mL) was added and the pH adjustment continued to 7–8. The phases were separated. The aqueous phase was extracted with additional ethyl acetate (2×500 mL). The combined rich ethyl acetate solution was washed with water (3×250 mL) and concentrated under reduced pressure to ~465 mL. This solution was carried through to the next oxidation step.

The rich ethyl acetate solution was charged from above into a three neck 1-L flask equipped with mechanical stirring, temperature controller, and addition funnel and cooled to 0–5° C. To the slurry, potassium bromide (1.53 g, 12.8 mmol) and TEMPO (2,2,6,6-tetramethyl-1-piperidinyloxy) (0.20 g, 1.28 mmol) were added. The pH of NaOCl (sodium hypochlorite) solution (212.1 mL) was adjusted to ~9.1 with saturated NaHCO$_3$ and added to the slurry at a rate such that the temperature remained at 0–5° C. Stirring was continued at 0–5° C. until the reaction was complete as determined by HPLC. The phases were separated and the aqueous phase was extracted with EtOAc (2×200 mL). The combined rich organic phase was washed with a 1:1 solution of sat. aq. Na$_2$S$_2$O$_3$ (sodium thiosulfate) (75 mL) and water (75 mL) followed by wash of the rich organic phase with 1N NaOH (250 mL). The rich organic phase was washed with water (250 mL) and concentrated to

34

~100 mL under reduced pressure. Isopropanol (IPA) (400 mL) was added and the resulting mixture was heated to reflux (80–85° C.). The solution was distilled to a volume of ~250 mL. Water (50 mL) was added and the crystal slurry was stirred at 70–80° C. for 1 h then allowed to cool to 20–25° C. over at least 1 h. The slurry was held at 20–25° C. for at least 1 h before collecting the solid by filtration on a Buchner funnel. The cake was washed with cold (0° C.) IPA/water (4:1) (2×50 mL) and dried to a constant weight under vacuum at 40° C. to afford 41.5 g (90%) of title aldehyde as a white crystalline solid.

EXAMPLE 3

Preparation of Olefin (6a)

Preparation of Olefin (6a)

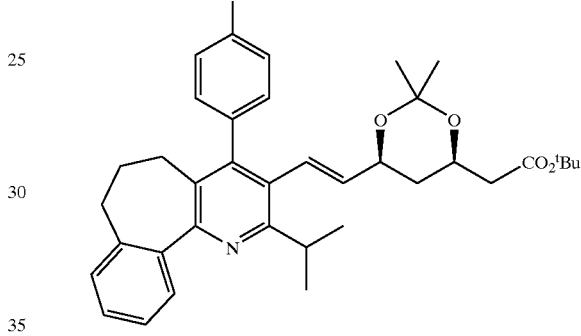

An N$_2$ purged 250 mL 3-neck rb flask was charged with Example 2 pyridine derivative (18) (5.0 g, 13.9 mmol), Example 1 sulfone (16) (6.92 g, 15.3 mmol) and THF (75 mL). The stirred solution was cooled to −74 to −78° C. Slowly a 1M solution of LiHMDS (lithium bis(trimethylsilyl)amide) (15.3 mL, 15.3 mmol) in THF was charged at a rate such that the temperature remained between −70 and ~78° C. After addition of the base was complete, the reaction mixture was warmed to ~−45° C. over ~15 minutes. The stirred reaction was quenched at ~70° C. by slow addition of sat. aq. NH$_4$Cl (7.5 mL) solution and water (38 mL). The dry ice bath was removed from the reaction mixture and the solution was warmed to 20–25° C. Ethyl acetate (50 mL) was added, the mixture agitated, and layers separated. The organic layer was washed with saturated sodium bicarbonate solution (2×38 mL) followed by brine (25 mL) and concentrated to a volume of 50 mL. Acetonitrile (50 mL) was added and the solution was concentrated to a volume of 50 mL. This step was repeated. Water (~5–6 mL) was slowly added to the hot solution (60–70° C.) until the cloud point was reached. The thin slurry was held for 30 min at high temperature and then slowly cooled over several hours with stirring. The product was filtered, cake was washed with a 5:1 mixture of acetonitrile and water, and dried to afford 7.5 g (91%) of the title compound as a white crystalline material.

EXAMPLE 4

Preparation of the Final Compound as Arginine Salt (18a)

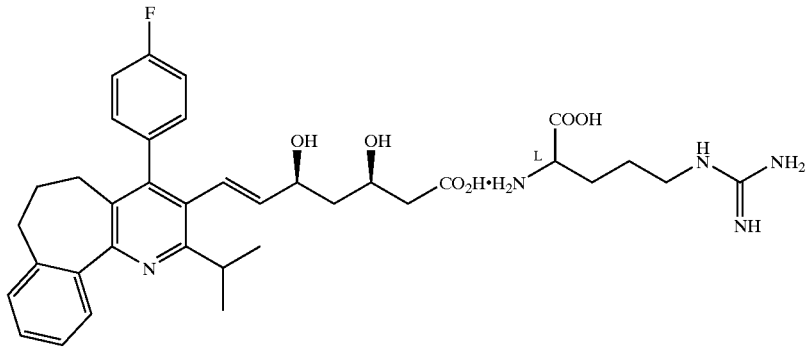

To a 3.0-liter round bottom flask equipped with a mechanical stirrer, a thermometer, and a septa was charged Example 3 trans olefin (92.0 g, 157 mmol) and THF (600 mL) at ambient temperature. With stirring, to the resulting clear sight yellow solution was added 6N HCl (aq. 74.6 mL, 447 mmol) at ambient temperature to form

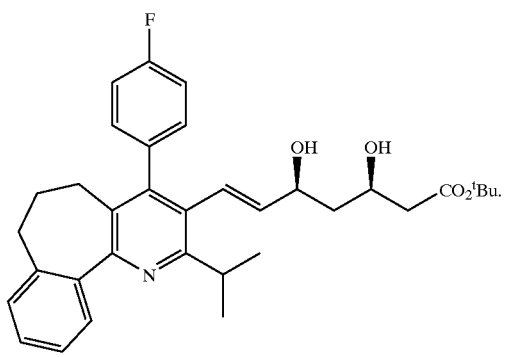

The reaction mixture was stirred for 5.0–6.0 h followed by addition of 2 N NaOH (aq. 389 mL, 777 mmol) to form a light yellow suspension. Agitation was maintained at ambient until reaction (saponification of (20)) was judged complete by an in-process HPLC assay. THF was evaporated on a rotary evaporator at about 45° C. The white slurry residue was diluted with 1000 mL of water and was extracted with MTBE (methyl t-butyl ether) (230 mL×2). After separating the MTBE layer, the aqueous layer containing

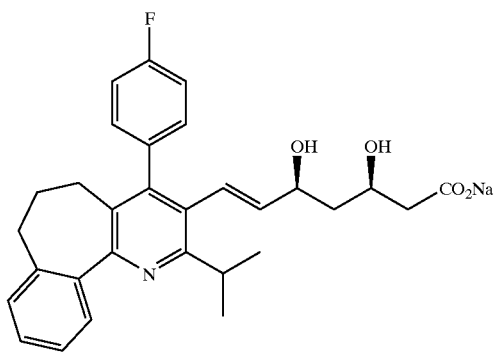

was transferred to a 5.0-liter round bottom flask equipped with a mechanical stirrer, a thermometer, and a septa. While temperature was controlled at <29° C., 1 N HCl (aq) was added to the above aqueous layer until the pH=6.94. Subsequently, 330 mL of ethyl acetate was added to the aqueous layer followed by charging more 1 N HCl (aq) until pH=2.82. After separating and saving the ethyl acetate layer, the aqueous layer was extracted with ethyl acetate (330 mL×3). The combined ethyl acetate layers containing the acid

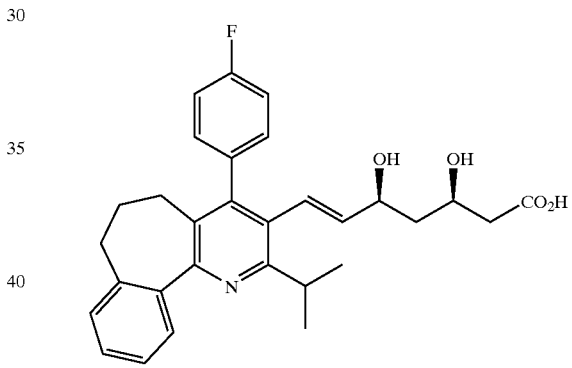

were washed with 50% brine (265 mL), brine (427 mL), separated and mixed with a suspension of L-arginine (27.4 g, 157 mmol) in ethanol (276 mL) and water (138 mL). The mixture was evaporated to dryness under reduced pressure at ca 45–50° C. To the resulting white solid were added ethyl acetate (450 mL), ethanol (316 mL), and water (145 mL) followed by heating the white suspension to 50° C. Another 36.7 mL of water was added to dissolve all solids at 56° C.; subsequently 1720 mL of ethyl acetate was added to the hot solution to initialize the crystallization. The white suspension was stirred at 50° C. for 1.5 h and at ambient for 13 h. After filtration, the crystalline solid was washed with 143 mL of a mixture of EtOAc (200 mL), EtOH (12 mL) and $H_2O$ (6 mL) and was dried in vacuo at 40–50° C. for 24 h. The title product obtained as a white solid weighed 78.9 (g). Yield, 75.7%. $[\alpha]^{25}_D$=+23.0 (c 0.31, $CH_3CN:H_2O$, 1:1, v/v).

$^1$H NMR ($CD_3OD$): δ 7.74 (dd, J=2.5 Hz, J'=1.0 Hz, 1H), 7.41 (dt, J=7.0 Hz, J'=6.1 Hz, 1H), 7.37 (dt, J=7.3 Hz, J'=1.4 Hz, 1H), 7.27 (d, J=7.2 Hz, 1H), 7.22 (dd, J=15.4 Hz, J'=7.0 Hz, 2H), 7.20 (d, J=7.0 Hz, 2H), 6.45 (d, J=16.5 Hz, 1H), 5.43 (dd, J=16.5 Hz, J'=6.5 Hz, 1H), 4.24 (q, J=6.5 Hz, 1H), 3.79 (m, 1H), 3.55–3.50 (m, 2H), 3.23 (m, 2H), 2.62 (t, J=7.2 Hz, 2H), 2.31–2.21 (m, 2H), 2.16 (t, J=6.8 Hz, 2H), 2.05 (m,

2H), 1.87 (q, J=7.0 Hz, 2H), 1.74 (m, 2H), 1.57 (m, 1H), 1.34 (d, J=6.8 Hz, 6H), 1.31 (m, 1H).

$^{13}$C NMR (CD$_3$OD) δ 180.1, 174.7, 164.5, 163.1, 162.5, 158.7, 157.8, 149.1, 141.9, 141.0, 140.8, 136.4, 132.6, 132.3, 131.6, 130.5, 130.1, 129.7, 129.2, 127.6, 126.6, 116.3, 116.0, 71.5, 68.0, 55.6, 45.0, 41.9,34.2, 33.1, 32.2, 29.6, 27.7, 25.8, 22.5.

MS: calc'd for C$_{36}$H$_{46}$FN$_5$O$_6$ (M$^+$+H) 490 and 175, found 490 and 175.

IR (KBr): 3341, 3200, 3070, 2960, 2934, 2860, 1670, 1629, 1602, 1580, 1509, 1465, 1450, 1397, 1357, 1221, 842, 766, 740 cm$^{-1}$.

Anal. Calc'd for C$_{36}$H$_{46}$FN$_5$O$_6$: C, 65.14, H, 6.98, N, 10.55. Found C, 65.15, H, 6.97, N, 10.53.

In addition, the following process modifications were employed to prepare the Example 4 L-arginine salt.

Process Modification A

Charge 100.00 (g) of olefin to a 1.0-liter 3-necked round-bottomed flask equipped with a mechanical stirrer, a thermometer, and septa. Charge 400 mL of THF (tetrahydrofuran) into the above flask. Agitate to provide a clear slightly yellow solution within 5-min. Charge ca. 6 N HCl aqueous solution (85.40 mL, 3.0 equiv.). Maintain agitation at ambient temperature until reaction is judged complete by an in-process HPLC assay. The reaction is complete when the area % (AP) of olefin is <1.00. Typical laboratory scale reaction times are 1–3 hours. Charge ca. 2 N NaOH (427.0 mL, 5.0 equiv.) aqueous solution to the above reaction mixture while maintaining the batch temperature <28° C. during addition. Maintain agitation at ambient temperature until reaction (saponification of the tert-butyl ester) is judged complete by an in-process HPLC assay. The reaction is complete when AP intermediate A is <0.5 in a HPLC assay. Typical laboratory scale reaction times are 5–20 h. Transfer the white slurry to a separatory funnel. Charge 1550 mL of water to the separatory funnel. Charge 500 mL MTBE (methyl t-butyl ether), shake the separatory funnel, and remove the MTBE upper layer. Phase separation took about 10–30 min to complete. Transfer the rich aqueous phase to a round-bottomed flask equipped with a mechanical stirrer and a pH meter. Charge ca. 1 N HCl aqueous solution to the above aqueous layer until to pH=5.6–7.6. Charge EtOAc (600 mL) to the aqueous mixture. Charge ca. 1 N HCl aqueous solution to the above mixture until about pH=2.2–3.2. Transfer the above acidic mixture to a separatory funnel, separate and retain the EtOAc upper phase. The residual aqueous layer was extracted with EtOAc (250 mL×2), separated, and the EtOAc layer was combined with the previous rich EtOAc phase. Wash the combined EtOAc layer with ca. 35% (wt./wt.) sodium chloride solution in water (400 mL×2), separate, and retain the EtOAc top layer. Filter the EtOAc solution containing intermediate 3 through a Buchner funnel equipped with a filter paper. Dilute the above EtOAc solution to 2.0 liter with EtOAc and obtain the weight of this solution (labeled solution A).

Charge L-Arginine (29.50 g, 0.99 equiv.) to a 4-liter jacketed glass reactor equipped with a mechanical agitator, a thermal couple, and two Teflon® stoppers. Charge 357.3 ml of EtOH to the above 4-liter reactor containing L-Arginine. Charge 160.5 ml of water to the above 4-liter reactor containing L-Arginine suspension. Heat the mixture to 50–55° C. to dissolve L-Arginine, hold the L-Arginine solution at 55–60° C. for 5 min. Charge the EtOAc solution labeled as solution A from earlier step to the reactor containing L-Arg solution at 55° C. Charge 450 mL of EtOAc to the above mixture. Heat the above solution to about 50–55° C. Maintain agitation at about 50° C. for 1.5–2.5 h. Cool the crystallization slurry to the ambient temperature in 4–5 h. After the heating is removed, the slurry should be agitated for additional 5.5–72 h. The solid was collected by filtration through a Buchner funnel equipped with a filter paper under reduced pressure. The crystals were washed with ca. 200 mL of a mixture of EtOAc (200 mL), EtOH (12 mL), and H$_2$O (6 mL). The white solid was dried in a vacuum oven at about <50° C. (oven set point) until the LOD<0.5% wt., this process typically takes 24–72 h to complete. The white solid weighed 102.10 (g) and was stored in an amber glass bottle in a drying cabinet.

Process Modification B

Charge 20.0 (g) of olefin to a 1.0-liter 3-necked round-bottomed flask equipped with a mechanical stirrer, a thermometer, and septa. Charge 80 mL of THF into the above flask. Agitate to provide a clear and slightly yellow-colored solution within 5-min. Charge ca. 6 N HCl aqueous solution (17.1 mL, 3.0 equiv.). Maintain agitation at ambient temperature until reaction is judged complete by an in-process HPLC assay. Charge ca. 2 N NaOH (85.4 mL, 5.0 equiv.) aqueous solution to the above reaction mixture while maintaining the batch temperature <28° C. during addition. Maintain agitation at ambient temperature until reaction (saponification of the tert-butyl ester) is judged complete by an in-process HPLC assay. Transfer the light yellow-colored emulsion to a separatory funnel. Charge 307.5 mL of water to the separatory funnel. Charge 50 mL MTBE, shake the separatory funnel, and remove the MTBE upper layer. Transfer the rich aqueous phase to a round-bottomed flask equipped with a mechanical stirrer and a pH meter. Charge ca. 1 N HCl aqueous solution to the above aqueous layer until to pH=5.6–7.6. Charge EtOAc (120 mL) to the aqueous mixture. Charge ca. 1 N HCl aqueous solution to the above mixture until about pH=2.5–3.5. Transfer the above acidic mixture to a separatory funnel, separate and retain the EtOAc upper phase. The residual aqueous layer was extracted with EtOAc (50 mL), separated, and the EtOAc layer was combined with the previous rich EtOAc phase. Wash the combined EtOAc layer with ca. 25% (wt./wt.) sodium chloride solution in water (400 mL×2), separate, and retain the EtOAc top layer. Dilute the above EtOAc solution to 400 mL with EtOAc and obtain the weight of this solution. Solution labeled as A.

Charge L-Arginine (5.71 g, 0.96 equiv.) to a 1-liter round-bottomed flask equipped with a mechanical agitator, a thermal couple, and a heating mantle or a water bath with a circulator. Charge 50.0 ml of EtOH to the above 1-liter reactor containing L-Arginine. Charge 32.57 ml of water to the above 4-liter reactor containing L-Arginine suspension. Heat the mixture to 50–55° C. to dissolve L-Arginine, hold the L-Arginine solution at 55–60° C. for 5 min. Transfer the hot L-Arginine solution to a reactor containing rich EtOAc solution-A from earlier step at the ambient temperature. Heat the resulting clear solution to 50–55° C. and hold at the temperature range for 20 min. Charge seeds (crystalline final compound) to the batch in the amount of 1% wt. of the input olefin. Maintain agitation at about 50–55° C. for 1.0 h. Charge slowly a mixture of EtOAc (100 mL) and EtOH (50 mL) over 2 h to the suspension. Upon completion of charging the EtOAc/EtOH mixture, agitate the resulting slurry for 1.0 h. Cool the batch to the ambient temperature in 2.0–6.0 h. Agitate the resulting white slurry at the ambient temperature for 1.0–18.0 h. The solid was collected by filtration through a Buchner funnel equipped with a filter paper under reduced pressure. The crystals were washed with ca. 60 mL of a mixture of EtOAc (200 mL), EtOH (12 mL), and H₂O (3 mL). The crystals were washed with ca. 60 mL of a mixture of EtOAc (100 mL), EtOH (100 mL). The white solid was dried in a vacuum oven at about <50° C. (oven set point) until the LOD<0.5% wt., this process typically takes 24–72 h to complete. The white solid weighed 21.0 (g) and was stored in an amber glass bottle in a drying cabinet.

Process Modification-C

Suspend olefin (3 g, 5.12 mmol) in 9 mL of isopropanol at room temperature. Add 6 N HCl (2.6 mL. 3 equiv.) streamwise into the suspension. Agitate and maintain the reaction mixture at ambient temperature. Monitor the reaction by HPLC. Raise the temperature to ~30–35° C. when the reaction is judged complete. Add 2N NaOH (12.8 mL, 5 equiv.) into the above warm reaction mixture while maintaining the batch temperature between 35–42° C. Hold the batch at about 40° C. for 2 h. Cool the batch and stir at rt overnight. Charge MTBE (30 mL) into the mixture. Adjust pH of the batch to 3.0–3.5 with 3N HCl (~3.5 mL). Separate the top organic layer. Wash the aqueous layer with MTBE (2×10 mL). Wash the combined organic layer with 50% brine (20 mL) followed by brine (20 mL). Polish filter the rich MTBE solution. Swap the solvent in the rich MTBE into IPA. Adjust the volume of the rich IPA solution to 85-mL (solution A).

Separately dissolve 0.845 g of L-Arginine in 5.6 mL of water at 55° C. Add 35 mL the rich IPA solution A to the L-Arginine solution at 55° C. Add 100 mg of seed crystals and then start adding the remaining rich IPA solution A dropwise over a period of 3–5 h. Cool the slurry to 50° over 10 min. Hold the slurry at 50° C. for 2 hour and cool to 20° C. over 6 hours. Hold the batch at 20° C. overnight. Filter the slurry and wash the wet cake with 8 mL of IPA. Dry the wet cake in a vacuum oven at 50° C. overnight. 3.06 g of white powder was obtained in 88.2% yield.

Process Modification D

To a 250 mL flask equipped with a magnetic stirrer was charged olefin (7 g, 11.95 mmoles), isopropyl alcohol (14 mL) and 6N HCl (6 mL, 3 molar eq., 35.85 mmoles). The mixture was stirred at room temperature (20–25° C.) and monitored for the disappearance of olefin (took about an hour). A solution of 2N NaOH (30 mL, 5 molar eq., 59.75 mmoles) was added in one portion to the flask, heated to 40° C. and monitored for the disappearance of the ester and lactone (0.5 to 1 h). The mixture was cooled to room temperature and the pH adjusted to 6–7 using 1N HCl (about 10–12 mL). At this point ethyl acetate was added to the mixture and the pH lowered to 3.5 (pH between 3 and 4) using 1N HCl. The mixture was transferred to a separatory funnel and the organic layer was separated and washed with 17% brine (2×35 mL).

To a 500 mL 3-necked flask equipped with a mechanical stirrer, temperature probe and septum was charged isopropyl alcohol (158 mL), 1 mole % of seed crystals and L-Arginine (1.98 g, 0.95 molar eq., 11.35 mmoles) of BMS 423526 and heated to 55–60° C. The ethyl acetate solution was then added to the mixture over 6–7 h (using a syringe pump), heated for 2 h at 55–60° C., cooled to room temperature and stirred for 12 h. The solids were filtered and washed with isopropyl alcohol (2 bed volumes). The solids were dried under house vacuum at 40–45° C. and a flow of nitrogen for 24 h. Yield: 6.73 g (89.3%)

EXAMPLE 5

Preparation of Pyridine Aldehyde (7a) (Scheme 2)

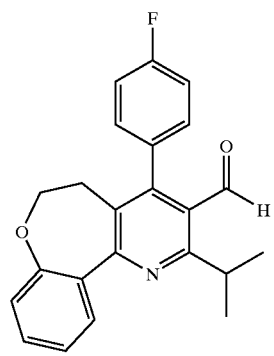

The title aldehyde may be prepared employing procedures set out in Example 2 and in reaction Scheme 2.

An example of a typical preparation of the aldehyde is set out below.

To a 500 mL round bottom flask equipped with a magnetic stirrer and a nitrogen inlet was charged compound (7b) (Scheme 2)

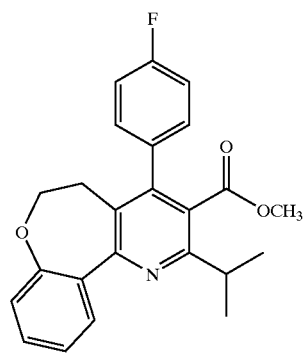

(50 g, 128.4 mmol) (prepared employing procedures similar to that described in Example 2) and toluene (170 mL). The mixture is stirred at 20–25° C. until a clear solution is obtained. A solution of 65% Red-Al in toluene (57.8 mL, 192.6 mmol) is added and the reaction mixture is heated to 80° C. until complete as determined by HPLC. The reaction mixture is cooled to 20° C. and quenched by pouring it into cold (0–5° C.) 20% HCl (495 mL). Phases are separated and the spent toluene phase is discarded. The pH of the aqueous phase is adjusted from <0 to 4–5 with lON NaOH. Ethyl acetate (500 mL) is added and the pH adjustment continued to 7–8. The phases are separated. The aqueous phase is extracted with additional ethyl acetate (2×500 mL). The combined rich ethyl acetate solution is washed with water (3×250 mL) and concentrated under reduced pressure to ~465 mL. This solution is carried through to the next oxidation step.

The rich ethyl acetate solution is charged from above into a three neck 1-L flask equipped with mechanical stirring, temperature controller, and addition funnel and cooled to 0–5° C. To the slurry, potassium bromide (1.53 g, 12.8 mmol) and TEMPO (2,2,6,6-tetramethyl-1-piperidinyloxy) (0.20 g, 1.28 mmol) are added. The pH of NaOCl (sodium hypochlorite) solution (212.1 mL) is adjusted to ~9.1 and added to the slurry at a rate such that the temperature remained at 0–5° C. Stirring is continued at 0–5° C. until the reaction is complete as determined by HPLC. The aqueous phase is extracted with EtOAc (2×200 mL). The combined rich organic phase is washed with a 1:1 solution of sat. aq. $Na_2S_2O_3$ (sodium thiosulfate) (75 mL) and water (75 mL) followed by wash of the rich organic phase with 1N NaOH (250 mL). The rich organic phase is washed with water (250 mL) and concentrated to 100 mL under reduced pressure. Isopropanol (IPA) (400 mL) is added and the resulting mixture is heated to reflux (80–85° C.). The solution is distilled to a volume of ~250 mL. Water (50 mL) is added and the crystal slurry is stirred at 70–80° C. for 1 h then allowed to cool to 20–25° C. over at least 1 h. The slurry is held at 20–25° C. for at least 1 h before collecting the solid by filtration on a Buchner funnel. The cake is washed with cold (0° C.) IPA/water (4:1) (2×50 mL) and dried to a constant weight under vacuum at 40° C. to afford title aldehyde.

EXAMPLE 6

Preparation of Olefin (19)

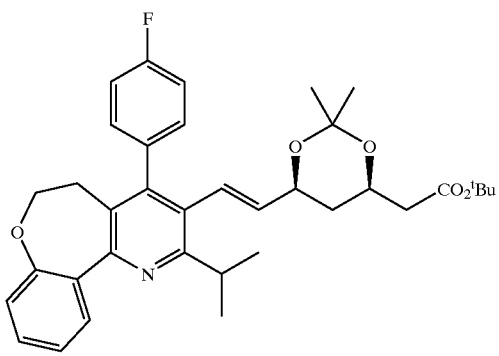

The title compound is prepared employing procedures set out in Example 3 and reaction Scheme 2 employing the Example 5 aldehyde and the Example 1 sulfone.

An example of a typical preparation of the Example 6 compound is set out below.

A $N_2$ purged 250 mL 3-neck rb flask is charged with Example 5 pyridine derivative (18) (5 g, 13.9 mmol), Example 1 sulfone (16) (6.9 g, 15.3 mmol) and THF (75 mL). The stirred solution is cooled to −74 to −78° C. Slowly a 1M solution of LiHMDS (lithium bis(trimethylsilyl) amide) (15.3 mL, 15.3 mmol) in THF is charged at a rate such that the temperature remained between −70 and −78° C. After addition of the base is complete, the reaction mixture is warmed to −−45° C. over ~15 minutes. The stirred reaction is quenched at −70° C. by slow addition of sat. aq. $NH_4Cl$ (7.5 mL) solution and water (38 mL). The dry ice bath is removed and the solution is warmed to 20–25° C. from the reaction mixture. Ethyl acetate (50 mL) is added, the mixture agitated, and layers separated. The organic layer is washed with saturated sodium bicarbonate solution (2×38 mL) followed by brine (25 mL) and concentrated to a volume of 50 mL. Acetonitrile (50 mL) is added and the solution is concentrated to a volume of 50 mL. This step is repeated. Water (~5–6 mL) is slowly added to the hot solution (60–70° C.) until the cloud point is reached. The thin slurry is held for 30 min at high temperature and then slowly cooled over several hours with stirring. The product is filtered, cake is washed with a 5:1 mixture of acetonitrile and water, and dried to afford the title compound.

EXAMPLE 7

Preparation of the Final Compound

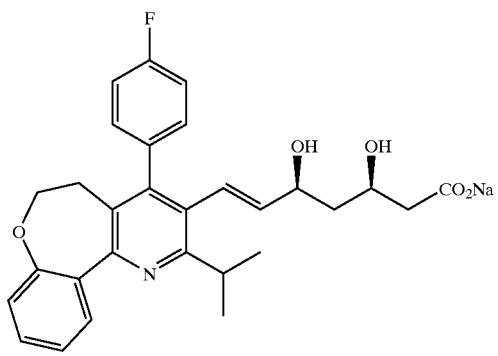

Following the procedure of Example 4, the Example 6 compound is employed to prepare the title compound in the form of the sodium salt.

What is claimed is:

1. A process for preparing a dihydroxy acid ester, salt, or free acid of the structure

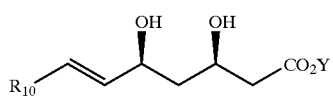

or the lactone thereof, wherein $R_{10}$ is the residue of an HMG CoA reductase inhibitor which is (a)

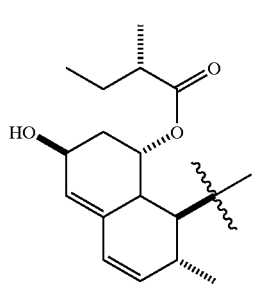

(b)

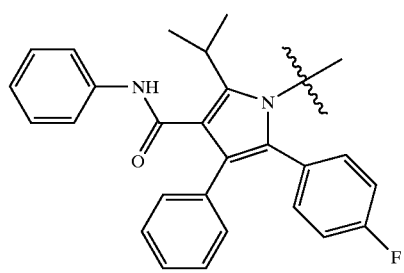

-continued (c) 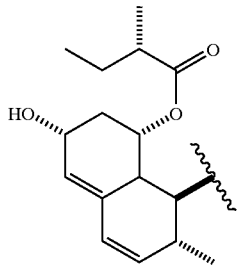

(d) 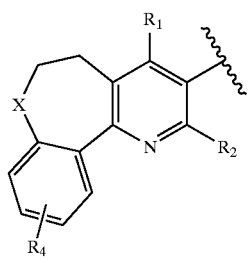

where

X is CH$_2$, O, S or NR$_7$;

R$_1$ and R$_2$ are the same or different and are independently selected from alkyl, arylalkyl, cycloalkyl, alkenyl, cycloalkenyl, aryl, heteroaryl or cycloheteroalkyl;

R$_4$ is H, halogen, CF$_3$, hydroxy, alkyl, alkoxy, alkanoylamino, aroylamino, or cyano;

R$_7$ is H, alkyl, aryl, alkanoyl, aroyl, or alkoxycarbonyl; and Y is alkyl, aryl, arylalkyl or CbZ, which comprises providing a trans olefin of the structure

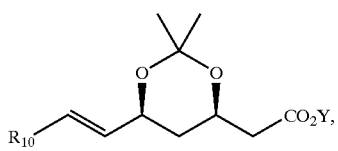

wherein R$_{10}$ and Y are as defined above, and subjecting the trans olefin to acidic conditions to remove the acetonide and form the dihydroxy acid ester;

optionally treating the dihydroxy acid with a base to form the corresponding salt;

optionally treating the dihydroxy acid salt with an acid to form the free acid of the structure

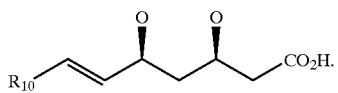

2. The process as defined in claim 1 where in the dihydroxy acid ester formed -continued

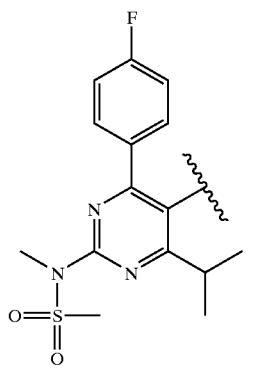

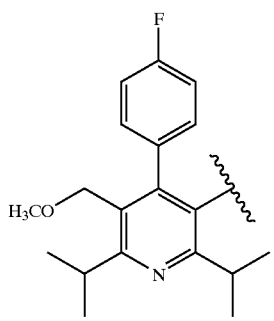

(e) 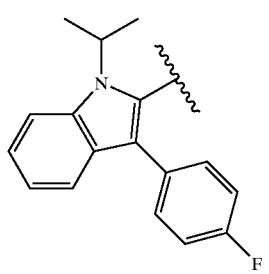

(f) 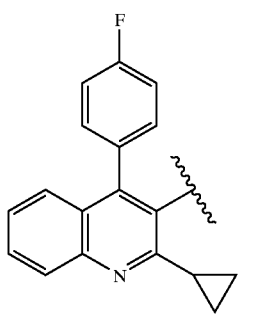

(g) 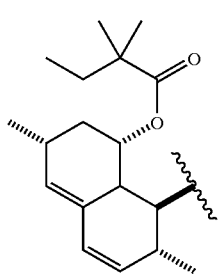

$R_{10}$ is

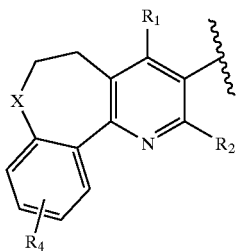 (i)

X is $CH_2$, $R_4$ is H, $R_1$ is p-F—$C_6H_5$ and $R_2$ is i-$C_3H_7$.

3. A process for preparing a diol ester compound of the structure

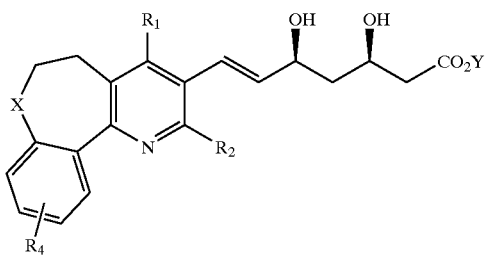

where

X is $CH_2$, O, S or $NR_7$;

Y is alkyl, aryl, arylalkyl or CbZ, $R_1$ and $R_2$ are the same or different and are independently selected from alkyl, arylalkyl, cycloalkyl, alkenyl, cycloalkenyl, aryl, heteroaryl or cycloheteroalkyl;

$R_4$ is H, halogen, $CF_3$, hydroxy, alkyl, alkoxy, alkanoylamino, aroylamino, or cyano;

$R_7$ is H, alkyl, aryl, alkanoyl, aroyl, or alkoxycarbonyl;

which comprises treating a pyridine carboxylaldehyde of the structure

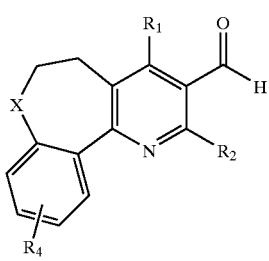

with a chiral sulfone of the structure

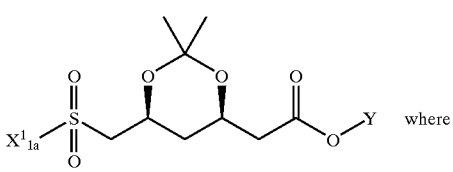 where

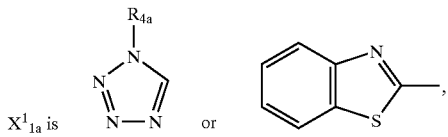

where $R_{4a}$ is aryl, alkyl, arylalkyl, or cycloalkyl, in the presence of a base to form a trans olefin of the structure

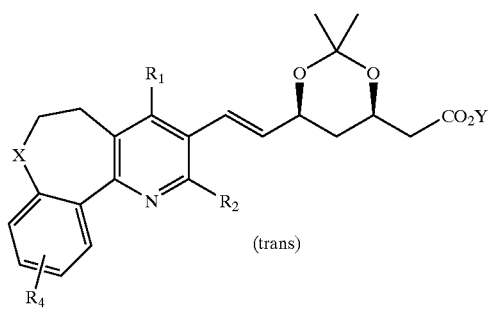

(trans)

and treating the trans olefin with an acid to form the diol of the structure

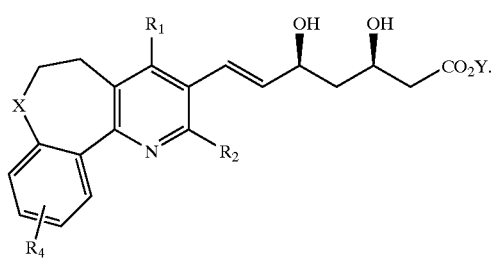

4. A process for preparing a dihydroxy acid or an ester, a salt, having the structure

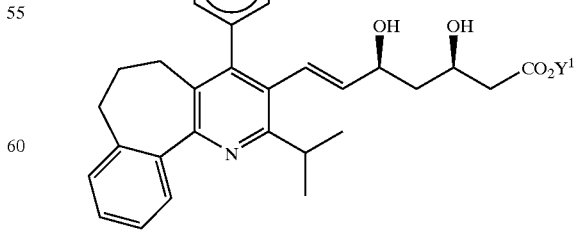

where $Y^1$ is H, alkyl or an alkali metal, or the lactone thereof which comprises providing a trans olefin of the structure

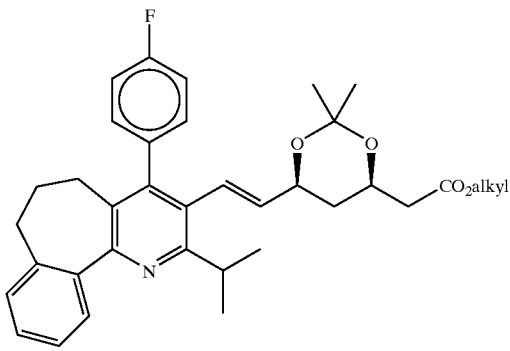

and treating the trans olefin with an acid to form a dihydroxy acid ester of the structure

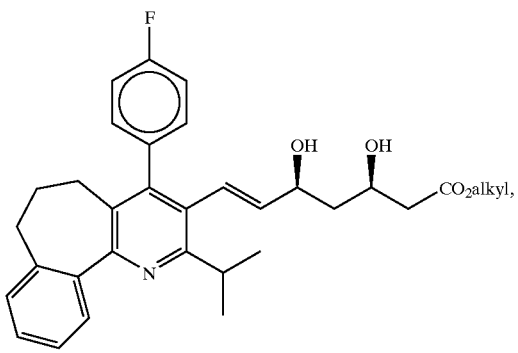

optionally treating the ester with a base to form the corresponding dihydroxy acid salt and optionally treating the salt with acid to form the corresponding free acid, and optionally treating the trans olefin with an acid to form the corresponding lactone.

5. A process for preparing a dihydroxy acid L-arginine salt having the structure

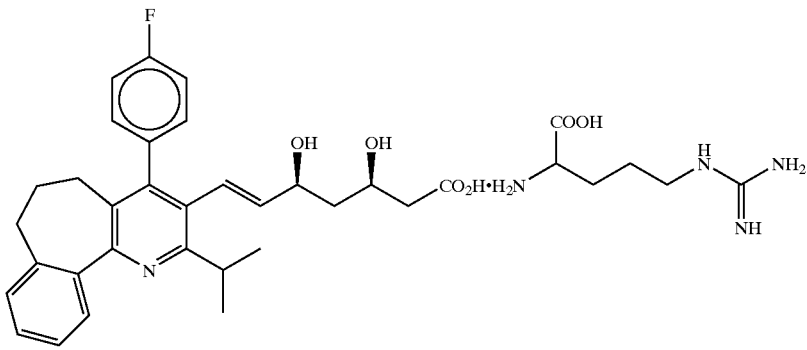

which comprises providing a trans olefin of the structure

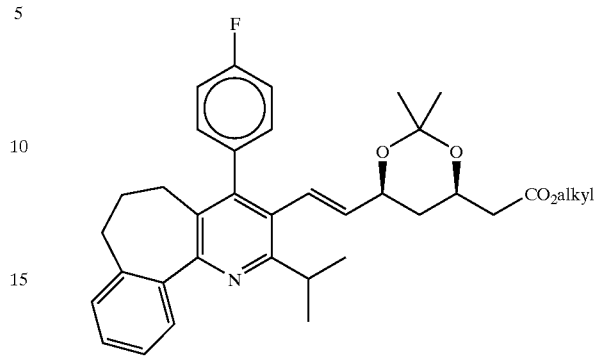

and treating the trans olefin with an acid to form a dihydroxy acid ester of the structure

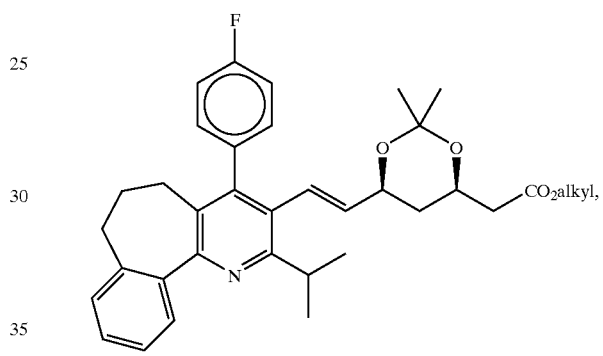

treating the ester with a base to form the corresponding dihydroxy acid salt, treating the salt with acid to form the corresponding free acid, and treating the free acid with L-arginine to form the corresponding L-arginine salt.

6. The process as defined in claim 5 further include the step of treating the free acid with L-arginine and seeds of the final dihydroxy acid L-arginine salt.

* * * * *

UNITED STATES PATENT AND TRADEMARK OFFICE
CERTIFICATE OF CORRECTION

PATENT NO. : 6,875,867 B2  
DATED : April 5, 2005  
INVENTOR(S) : Paul R. Brodfuehrer et al.

It is certified that error appears in the above-identified patent and that said Letters Patent is hereby corrected as shown below:

Column 9,  
Line 66, change " ╲ " to -- ╲╲ --.

Column 21,  
Line 11, change "MCPBA" to -- mCPBA --.

Column 31,  
Line 22, move "A" from line 22 to line 40.

Column 40,  
Line 53, change "ION" to -- 10N --.

Column 44,  
Lines 60-64, change the formula " 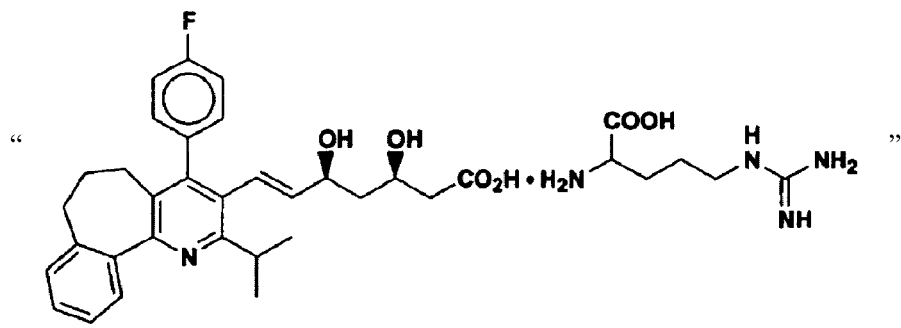 " to read

-- 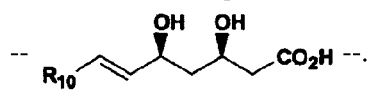 --.

Columns 47 to 48  
Line 44, change the formula

" 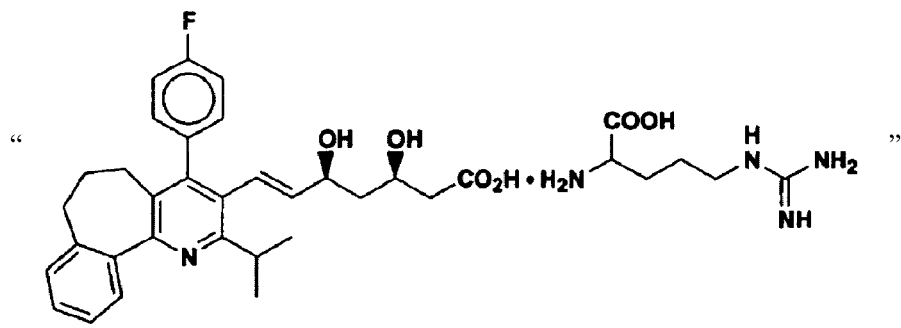 "

to read

-- 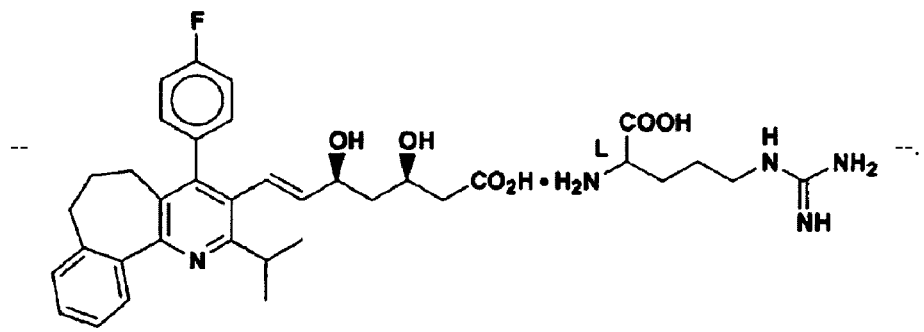 --.

UNITED STATES PATENT AND TRADEMARK OFFICE
CERTIFICATE OF CORRECTION

PATENT NO. : 6,875,867 B2
DATED : April 5, 2005
INVENTOR(S) : Paul R. Brodfuehrer et al.

It is certified that error appears in the above-identified patent and that said Letters Patent is hereby corrected as shown below:

Column 48,
Lines 22-36, change the formula

" 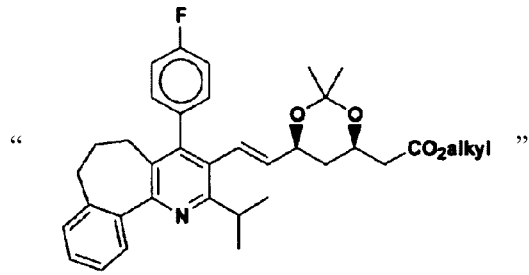 "

to read

-- 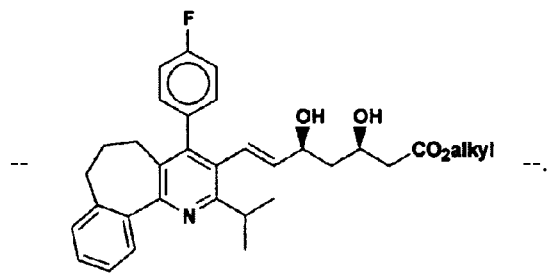 --.

Signed and Sealed this

Twenty-second Day of November, 2005

JON W. DUDAS
*Director of the United States Patent and Trademark Office*